United States Patent
Travins et al.

(10) Patent No.: US 9,724,350 B2
(45) Date of Patent: Aug. 8, 2017

(54) N,6-BIS(ARYL OR HETEROARYL)-1,3,5-TRIAZINE-2,4-DIAMINE COMPOUNDS AS IDH2 MUTANTS INHIBITORS FOR THE TREATMENT OF CANCER

(71) Applicant: Agios Pharmaceuticals, Inc., Cambridge, MA (US)

(72) Inventors: Jeremy Travins, Southborough, MA (US); Luke Utley, Milford, NH (US)

(73) Assignee: Agios Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/904,032

(22) PCT Filed: Jul. 10, 2014

(86) PCT No.: PCT/US2014/046204
§ 371 (c)(1),
(2) Date: Jan. 8, 2016

(87) PCT Pub. No.: WO2015/006592
PCT Pub. Date: Jan. 15, 2015

(65) Prior Publication Data
US 2016/0158241 A1    Jun. 9, 2016

Related U.S. Application Data

(60) Provisional application No. 61/845,352, filed on Jul. 11, 2013.

(51) Int. Cl.
| | |
|---|---|
| C07D 251/48 | (2006.01) |
| C07D 403/04 | (2006.01) |
| C07D 403/12 | (2006.01) |
| C07D 403/14 | (2006.01) |
| C07D 401/04 | (2006.01) |
| C07D 401/12 | (2006.01) |
| C07D 401/14 | (2006.01) |
| C07D 413/12 | (2006.01) |
| C07D 417/12 | (2006.01) |
| C07D 417/14 | (2006.01) |
| A61K 31/53 | (2006.01) |
| A61P 35/00 | (2006.01) |
| C07D 251/18 | (2006.01) |
| A61K 45/06 | (2006.01) |

(52) U.S. Cl.
CPC .............. *A61K 31/53* (2013.01); *A61K 45/06* (2013.01); *C07D 251/18* (2013.01); *C07D 401/04* (2013.01); *C07D 401/12* (2013.01); *C07D 401/14* (2013.01); *C07D 403/04* (2013.01); *C07D 403/12* (2013.01); *C07D 413/12* (2013.01); *C07D 417/12* (2013.01); *C07D 417/14* (2013.01)

(58) Field of Classification Search
CPC .. C07D 251/48; C07D 403/04; C07D 403/14; C07D 401/04; C07D 401/14; A61K 31/53; A61K 45/06
USPC .......................... 544/194, 204, 208; 514/245
See application file for complete search history.

(56) References Cited

U.S. PATENT DOCUMENTS

| | | | |
|---|---|---|---|
| 2,390,529 | A | 12/1945 | Friedheim |
| 3,755,322 | A | 8/1973 | Winter et al. |
| 3,867,383 | A | 2/1975 | Winter |
| 4,084,053 | A | 4/1978 | Desai et al. |
| 4,693,726 | A | 9/1987 | Meininger et al. |
| 5,489,591 | A | 2/1996 | Kobayashi et al. |
| 6,274,620 | B1 | 8/2001 | Labrecque et al. |
| 7,173,025 | B1 | 2/2007 | Stocker et al. |
| 7,858,782 | B2 | 12/2010 | Tao et al. |
| 8,133,900 | B2 | 3/2012 | Hood et al. |
| 8,465,673 | B2 | 6/2013 | Yasuda et al. |
| 2003/0109527 | A1 | 6/2003 | Jin et al. |
| 2003/0213405 | A1 | 11/2003 | Harada et al. |
| 2006/0084645 | A1 | 4/2006 | Pal et al. |
| 2007/0244088 | A1 | 10/2007 | Brickmann et al. |

(Continued)

FOREIGN PATENT DOCUMENTS

| | | |
|---|---|---|
| CN | 101575408 | 11/2009 |
| CN | 102659765 | 9/2012 |
| CN | 103097340 | 5/2013 |
| DE | 3314663 | 10/1983 |
| DE | 3512630 | 10/1986 |

(Continued)

OTHER PUBLICATIONS

Koshelev et al. Russian Journal of Organic Chemistry, 21(2) 291-294, 1995.*

(Continued)

*Primary Examiner* — Vankataraman Balasubramanian
(74) *Attorney, Agent, or Firm* — Jones Day

(57) ABSTRACT

Provided are compounds of formula (I), Wherein: ring A and ring B are each independently an optionally substituted 5-6 membered monocyclic aryl or heteroaryl. The compounds are inhibitors of isocitrate dehydrogenase 2 (IDH2) mutants useful for treating cancer.

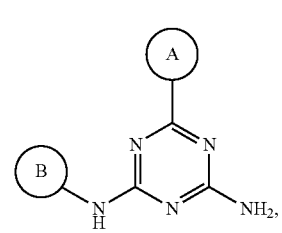

(I)

14 Claims, No Drawings

(56) References Cited

U.S. PATENT DOCUMENTS

| | | |
|---|---|---|
| 2009/0093526 A1 | 4/2009 | Miller et al. |
| 2009/0163508 A1 | 6/2009 | Kori et al. |
| 2009/0163545 A1 | 6/2009 | Goldfarb |
| 2010/0129350 A1 | 5/2010 | Zacharie et al. |
| 2010/0144722 A1 | 6/2010 | Alexander et al. |
| 2011/0073007 A1 | 3/2011 | Yasuda et al. |
| 2011/0288065 A1 | 11/2011 | Fujihara et al. |
| 2012/0164143 A1 | 6/2012 | Teeling et al. |
| 2012/0202818 A1 | 8/2012 | Tao et al. |
| 2012/0238576 A1 | 9/2012 | Tao et al. |
| 2012/0277233 A1 | 11/2012 | Tao et al. |
| 2013/0035329 A1 | 2/2013 | Saunders et al. |
| 2013/0183281 A1 | 7/2013 | Su et al. |
| 2013/0184222 A1 | 7/2013 | Popovici-Muller et al. |
| 2013/0190249 A1 | 7/2013 | Lemieux et al. |
| 2013/0190287 A1 | 7/2013 | Cianchetta et al. |
| 2013/0197106 A1 | 8/2013 | Fantin et al. |
| 2013/0316385 A1 | 11/2013 | Cantley et al. |
| 2014/0187435 A1 | 7/2014 | Dang et al. |
| 2014/0206673 A1 | 7/2014 | Cao et al. |
| 2014/0213580 A1 | 7/2014 | Cao et al. |
| 2015/0018328 A1 | 1/2015 | Konteatis et al. |
| 2015/0031627 A1 | 1/2015 | Lemieux et al. |
| 2015/0087600 A1 | 3/2015 | Popovici-Muller et al. |
| 2015/0240286 A1 | 8/2015 | Dang et al. |

FOREIGN PATENT DOCUMENTS

| | | |
|---|---|---|
| EP | 0945446 | 9/1999 |
| JP | 11158073 | 6/1999 |
| JP | 2004107220 | 4/2004 |
| JP | 2009237115 | 10/2009 |
| JP | 2010079130 | 4/2010 |
| JP | 2010181540 | 8/2010 |
| JP | 4753336 | 8/2011 |
| WO | WO 02102313 | 12/2002 |
| WO | WO 03016289 | 2/2003 |
| WO | WO 2004009562 | 1/2004 |
| WO | WO 2004046120 | 6/2004 |
| WO | WO 2004050033 | 6/2004 |
| WO | WO 2005035507 | 4/2005 |
| WO | WO 2005060956 | 7/2005 |
| WO | WO 2005065691 | 7/2005 |
| WO | WO 2006079791 | 8/2006 |
| WO | WO 2008070661 | 6/2008 |
| WO | WO 2008076883 | 6/2008 |
| WO | WO 2008154026 | 12/2008 |
| WO | WO 2009/118567 | 10/2009 |
| WO | WO 2010/105243 | 9/2010 |
| WO | WO 2011005210 | 1/2011 |
| WO | WO 2012074999 | 6/2012 |
| WO | WO 2012160034 | 11/2012 |
| WO | WO 2012171506 | 12/2012 |
| WO | WO/2012173682 | 12/2012 |
| WO | WO 2013102431 | 7/2013 |
| WO | WO 2013107291 | 7/2013 |
| WO | WO 2013107405 | 7/2013 |
| WO | WO 2013133367 | 9/2013 |

OTHER PUBLICATIONS

Kelarev et al. "Synthesis and properties of sym-triazines. 10 Synthesis of 2,4-diamino-sym-triazines containing a sterically hindered phenol substituent" Chemistry of Heterocyclic Compounds (1992) Vol28, No. 10, pp. 1189-1193.*

Krell et al., Future Oncol. (2013) 9(12), 1923-1935.*

Reitman et al., J Natl Cancer Inst 2010;102:932-941.*

Cairns et al., Cancer Discov; 3(7); 730-41,2013.*

Cecil Textbook of Medicine, edited by Bennet, J.C., and Plum F., 20th edition,vol. 1, 1004-101 O, 1996.*

Freshney et al.,Culture of Animal Cells, a Manual of Basic Technique, Alan R. Liss, Inc., 1983, New York, p. 4.*

Dermer et al., Bio/Technology, 1994, 12:320.*

Golub et al., Science, 286, 531-537, 1999.*

Ansell et al. "The interactions of artificial coenzymes with alcohol dehydrogenase and other NAD(P)(H) dependent enzymes" Journal of Molecular Catalysis B: Enzymatic (1999) vol. 6, No. 1-2, pp. 111-123.

Baker Botts "In print-reac throught claims" attorney's practice profiles news and events (2002).

Bhushan et al. "Reversed-phase liquid chromatographic resolution of diastereomers of protein and non-protein amino acids prepared with newly synthesized chiral derivatizing reagents based on cyanuric chloride" Amino Acids (2011) vol. 40, pp. 403-409.

Braun et al. "Triazine-based polymers: 4. MALDI-MS of triazine-based polyamines" Polymer (1996) vol. 37, No. 5, pp. 777-783.

Cairns et al. "Oncogenic Isocitrate Dehydrogenase Mutations: Mechanisms, Models, and Clinical Opportunities" Cancer Discovery (2013) vol. 3, Iss 7, pp. 730-741.

Cecil Textbook of Medicine, edited by Bennet and Plum, (1997) 20th edition, vol. 1, pp. 1004-1010.

Chan et al. "Multi-domain hydrogen-bond forming metal chelates: X-ray crystal structures of dicyclopalladated 2,3-bis[6-(2-amino-4-phenylamino-1 ,3,5-triazinyl)]pyrazine (H2L) [Pd2Br2L] and 2,6-bis[6-(2-amino-4-phenylamino-1,3,5-triazinylium)]-pyridine dichloride" Chemical Communications (1996) No. 1, pp. 81-83.

Chapman et al. "Substituted aminopyrimidine protein kinase B (PknB) inhibitors show activity against *Mycobacterium tuberculosis*" Bioorganic & Medicinal Chemistry Letters (2012) vol. 22, pp. 3349-3353.

Chen et al. "Cytotoxicity, Hemolysis, and Acute in Vivo Toxicity of Dendrimers Based on Melamine, Candidate Vehicles for Delivery" J. Am. Chem. Soc. (2004) vol. 126, No. 32, pp. 10044-10048.

Dang et al. "IDH Mutations in Glioma and Acute Myeloid Leukemia" Trends in Molecular Medicine (2010) vol. 16, No. 9, pp. 387-397.

Dermer "another Anniversary for the War on Cancer" Bio/Technology (1994) vol. 12, p. 320.

Dohner et al. "Impact of Genetic Features on Treatment Decisions in AML" American Society of Hematology (2011) pp. 36-42.

Dorwald, "Side reactions in organic synthesis," Wiley: VCH, Weinheim, p. IX (2005).

Duanmu et al. "Dendron-Functionalized Superparamagnetic Nanoparticles with Switchable Solubility in Organic and Aqueous Media: Matriced for Homogeneous Catalysis and Potential MRI Contrast Agents" Chem. Mater. (2006) vol. 18, No. 25, pp. 5973-5981.

European Search Report for European Application No. 12799802.9 dated Sep. 24, 2014.

European Search Report for European Application No. EP 12800001.5 dated Oct. 10, 2014.

Freshney et al. "Culture of Animal Cells, A Manual of Basic Techniques" Alan R. Liss, Inc. (1983) pp. 1-6.

Gewald et al. "Discovery of triazines as potent, selective and orally active PDE4 inhibitors" Bioorganic & medicinal Chemistry Letters (2013) vol. 23, pp. 4308-4314.

Golub et al. "Molecular Classification of Cancer: Class Discovery and Class Prediction by Gene Expression Monitoring" Science (1999) vol. 286, pp. 531-537.

International Preliminary Report on Patentability for PCT/CN2012/000841 dated Dec. 17, 2013.

International Preliminary Report on Patentability for PCT/CN2012/077096 dated Dec. 17, 2013.

International Preliminary Report on Patentability for PCT/US2011/030692 dated Oct. 2, 2012.

International Search Report and Written Opinion for International Application No. PCT/CN2013/080105 dated Jul. 11, 2014.

International Search Report and Written Opinion for International Application No. PCT/CN2013/081170 dated Apr. 30, 2014.

International Search Report and Written Opinion for International Application No. PCT/CN2014/081957 dated Sep. 30, 2014.

International Search Report and Written Opinion for International Application No. PCT/CN2014/081958 dated Sep. 29, 2014.

International Search Report and Written Opinion for International Application No. PCT/US2014/046202 dated Sep. 30, 2014.

(56) References Cited

OTHER PUBLICATIONS

International Search Report and Written Opinion for International Application No. PCT/US2014/049469 dated Jan. 22, 2015.
International Search Report and Written Opinion for International Application No. PCT/CN2014/082869 dated Sep. 30, 2014.
International Search Report for International Application No. PCT/CN2013/079184 dated Jan. 12, 2015.
International Search Report for International Application No. PCT/CN2013/079200 dated Jan. 12, 2015.
International Search Report for International Application No. PCT/US2014/046204 dated Oct. 1, 2014.
International Search Report for PCT/US2013/064601 dated Feb. 24, 2014.
Irikura et al. "New s-Triazine Derivatives as Depressants for Reticuloendothelial Hyperfunction Induced by Bacterial Endotoxin" Journal of Medicinal Chemistry (1970) vol. 13, pp. 1081-1089.
Kaila et al. "A convenient one-pot synthesis of trisubstituted 1,3,5-triazines through intermediary amidinothioureas" Tetrahedron Letters (2010) vol. 51, pp. 1486-1489.
Kelarev et al. "Synthesis and properties of sym-triazines. 10 Synthesis of 2,4-diamino-sym-triazines containing a sterically hindered phenol substituent" Chemistry of Heterocyclic Compounds (1992) vol. 28, No. 10, pp. 1189-1193.
Koshelev et al. "Synthesis of 1-3,7 N-substituted 2,4-diamino-1,3,5-triazines containing pyridyl groups" Russian Journal of Organic Chemistry (1995) vol. 31, No. 2, pp. 260-263.
Krell et al., "IDH mutations in tumorigenesis and their potential role as novel therapeutic targets" Future Oncology (2013) vol. 9, Iss 12, pp. 1923-1935.
Kusakabe et al. Chemical Abstracts vol. 152, No. 191956, Abstract for WO2010007756 (2010).
Lee et al. "Combinatorial Solid-Phase Synthesis of 6-Aryl-1,3,4-triazines via Suzuki Coupling" Aust. J. Chem. (2011) vol. 64, pp. 540-544.
Madsen-Duggan et al. "Lead optimization of 5.6-diarylpyridines as CB1 receptor inverse agonists" Bioorganic & Medicinal Chemistry Letters (2007) vol. 17, pp. 2031-2035.
Moreno et al. "Identification of diamine linkers with differing reactivity and their applicationin the synthesis of melamine dendrimers" Tetrahedron Letters (2008) vol. 49, pp. 1152-1154.
Moreno et al. "Molecular recognition in dendrimers based on melamine" Polymer Preprints (2005) vol. 46, No. 2, pp. 1127.
Pubchem CID 4078245 [online]; Sep. 13, 2005 [retrieved on Feb. 4, 2012]; retrieved from http://pubchem.ncbi.nim.nih.gov/; 2d-structure.
Pubchem CID 4854170 [online]; Sep. 17, 2005 [retrieved on Feb. 4, 2012]; retrieved from http://pubchem.ncbi.nim.nih.gov/; 2d-structure.
Raynaud et al. "Absence of R140Q Mutation of Isocitrate Dehydrogenase 2 in Gliomas and Breast Cancers" Oncology Letters (2010) vol. 1, No. 5, pp. 883-884.
Scharn et al. "Spatially Addressed Synthesis of Amino- and Amino-Oxy-Substituted 1,3,5-Triazine Arrays on Polymeric Membranes" Journal of Combinatorial Chemistry (2000) vol. 2, No. 4, pp. 361-369.
Shih et al. "The Role of Mutations in Epigenetic Regulators in Myeloid Malignancies" Nature Reviews Cancer (2012) vol. 12, No. 9, pp. 599-612.
STN File CA, Registry No. 380466-24-0 entered STN on Jan. 4, 2002, Chemical Abstracts Index Name "Benzenesulfonamide, N-methyl-N-phenyl-3-[[4-(2-pyridinyl)-1-piperazinyl]carbonyl]".
STN File CA, Registry No. 713505-78-3, entered STN on Jul. 21, 2004, Chemical Abstracts Index Name "1-Piperazinecarboxylic acid, 4-[4-methyl-3-[(phenylamino)sulfonyl]benzoyl]-, ethyl ester".
STN File CA, Registry No. 736168-79-9 entered STN on Aug. 31, 2004, Chemical Abstracts Index Name "Benzenesulfonamide, 3,4-difluoro-N-[3-334-(phenylmethyl0-1-piperazinyl]carbonyl]phenyl".
STN File CA, Registry No. 847757-57-7, entered STN on Apr. 1, 2005, Chemical Abstracts Index Name "Benzenesulfonamide, 3-[[4-(1,3-benzodioxol-5-ylmethyl)-1-piperazinyl]carbonyl]-N-(4-ethoxyphenyl)-N,4-dimethyl-" or "Piperazine, 1-(1,3-benzodioxol-5-ylmethyl)-4-[5-[[(4-ethoxyphenyl)methylamino]sulfonyl]-2-methylbenzoyl]-".
STN Registry, L23 Answer 2 of 3 (CAS No. 1032450-21-7), Database: ASINEX Ltd.,Entered STN: Jul. 3, 2008 (Jul. 3, 2008).
STN Registry. L23 Answer 1 of 3 (CAS No. 1038821-72-5),Database: ChemDB (University of California Irvine), Entered STN: Aug. 5, 2008 (Aug. 5, 2008).
Struys et al. "Investigations by mass isotopomer analysis of the formation of D-2- hydroxyglutarate by cultured lymphoblasts from two patients with D-2-hydroxyglutaric aciduria" FEBS Letters (2004) vol. 557, pp. 115-120.
Struys et al. "Mutations in the D-2-hydroxyglutarate dehydrogenase gene cause D-2-hydroxyglutaric aciduria" American Journal of Human Genetics (2005) vol. 76, pp. 358-360.
Supplementary European Search Report for EP 10751525 Mailed Dec. 14, 2012.
Supplementary European Search Report for EP Application No. 10825707.2 dated Jun. 28, 2013.
Takagi et al. "Synthesis of poly(triazinylstyrene) containing nitrogen-bawed ligand and function as metal ion adsorbent and oxidation catalyst" Reactive & Functional Polymers (2006) vol. 31, pp. 1718-1724.
Thompson, "Metabolic Enzymes as Oncogenes or Tumor Suppressors." The New England Journal of Medicine (2009) vol. 360, No. 8, pp. 813-815.
Van Schaftingen et al. "L-2-Hydroglutaric aciduria, a disorder of metabolite repair" J Inherit. Metab. Dis. (2009) vol. 32, pp. 135-142.
Wang et al "Facile Synthesis of 2,4-Dianiino-6-alkyi- or 6-Aryl-Pyrimidine Derivatives" Journal of Heterocyclic Chemistry (2010) vol. 47 pp. 1056-1061.
Wang et al. "Targeted Inhibition of Mutant IDH2 in Leukemia Cells Induces Cellular Differentiation" Science (2013) vol. 340, Issue 6132, pp. 622-626.
Wang et al. "A novel ligand N,N'-di(2-pyridyl)-2,4-diamino-6-phenyl-1,3,5-triazine (dpdapt) and its complexes: [Cu(dpdapt)C12] and [Cu(dpdapt)(NO3)(H2O)] • NO3 • H2O" Polyhedron (2006) vol. 25, No. 1, pp. 195-202.
Ward et al. "The Common Feature of Leukemia-Associated IDH1 and IDH2 Mutations Is a Neomorphic Enzyme Activity Converting [alpha]-Ketoglutarate to 2-Hydroxyglutarate" Cancer Cell (2010) vol. 17, No. 3 pp. 225-234.
Watanabe et al., "IDH1 Mutations Are Early Events in the Development of Astrocytomas and Oligodendrogliomas". American Journal of Pathology (2009) vol. 174, No. 4, pp. 1149-1153.
Written Opinion for PCT/US2010/027253 mailed Aug. 19, 2010.
Written Opinion of International Search Authority for PCT/CN2013/000009 dated Apr. 18, 2013.
Written Opinion of Search Authority for PCT/US2010/53623 dated Jan. 18, 2011.
Written Opinion of the International Searching Authority for PCT/US2011/067752 dated Mar. 5, 2012.
Yan et al., "IDH1 and IDH2 Mutations in Gliomas." The New England Journal of Medicine, (2009) vol. 360, No. 8, pp. 765-773.
Zhao et al. "Glioma-derived mutations in IDH1 dominantly inhibit IDH1 catalytic activity and induce HIF-1alpha", Science (2009) vol. 324, No. 5924, pp. 261-265.

\* cited by examiner

N,6-BIS(ARYL OR HETEROARYL)-1,3,5-TRIAZINE-2,4-DIAMINE COMPOUNDS AS IDH2 MUTANTS INHIBITORS FOR THE TREATMENT OF CANCER

This application is a 371 of international application No. PCT/US2014/046204, filed Jul. 10, 2014, which claims priority from U.S. Application Ser. No. 61/845,352 filed Jul. 11, 2013, which are incorporated herein by reference in their entireties.

CLAIM OF PRIORITY

This application claims priority from U.S. Application Ser. No. 61/845,352 filed Jul. 11, 2013, which is incorporated herein by reference in its entirety.

BACKGROUND OF INVENTION

Isocitrate dehydrogenases (IDHs) catalyze the oxidative decarboxylation of isocitrate to 2-oxoglutarate (i.e., α-ketoglutarate). These enzymes belong to two distinct subclasses, one of which utilizes NAD(+) as the electron acceptor and the other NADP(+). Five isocitrate dehydrogenases have been reported: three NAD(+)-dependent isocitrate dehydrogenases, which localize to the mitochondrial matrix, and two NADP(+)-dependent isocitrate dehydrogenases, one of which is mitochondrial and the other predominantly cytosolic. Each NADP(+)-dependent isozyme is a homodimer.

IDH2 (isocitrate dehydrogenase 2 (NADP+), mitochondrial) is also known as IDH; IDP; IDHM; IDPM; ICD-M; or mNADP-IDH. The protein encoded by this gene is the NADP(+)-dependent isocitrate dehydrogenase found in the mitochondria. It plays a role in intermediary metabolism and energy production. This protein may tightly associate or interact with the pyruvate dehydrogenase complex. Human IDH2 gene encodes a protein of 452 amino acids. The nucleotide and amino acid sequences for IDH2 can be found as GenBank entries NM_002168.2 and NP_002159.2 respectively. The nucleotide and amino acid sequence for human IDH2 are also described in, e.g., Huh et al., Submitted (November-1992) to the EMBL/GenBank/DDBJ databases; and The MGC Project Team, Genome Res. 14:2121-2127(2004).

Non-mutant, e.g., wild type, IDH2 catalyzes the oxidative decarboxylation of isocitrate to α-ketoglutarate (α-KG) thereby reducing $NAD^+$ ($NADP^+$) to NADH (NADPH), e.g., in the forward reaction:

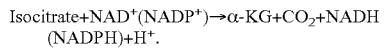

Isocitrate+$NAD^+$($NADP^+$)→α-KG+$CO_2$+NADH (NADPH)+$H^+$.

It has been discovered that mutations of IDH2 present in certain cancer cells result in a new ability of the enzyme to catalyze the NADPH-dependent reduction of α-ketoglutarate to R(−)-2-hydroxyglutarate (2HG). 2HG is not formed by wild-type IDH2. The production of 2HG is believed to contribute to the formation and progression of cancer (Dang, L et al, Nature 2009, 462:739-44).

The inhibition of mutant IDH2 and its neoactivity is therefore a potential therapeutic treatment for cancer. Accordingly, there is an ongoing need for inhibitors of IDH2 mutants having alpha hydroxyl neoactivity.

SUMMARY OF INVENTION

Described herein are compounds of Structural Formula I, or a pharmaceutically acceptable salt or hydrate thereof:

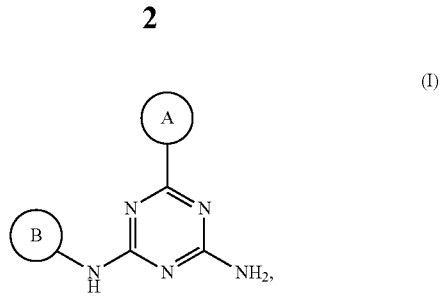

(I)

wherein:
ring A is an optionally substituted 5-6 member monocyclic aryl or monocyclic heteroaryl; and
ring B is an optionally substituted 5-6 member monocyclic aryl or monocyclic heteroaryl; wherein:
a. ring A and ring B are not both an optionally substituted 6 member monocyclic aryl;
b. when ring A is unsubstituted pyridyl, then ring B is not phenyl optionally substituted with one to three groups independently selected from methyl, ethyl, t-butyl, methoxy, $CH(OH)CH_3$, Cl, Br, SH, and $CF_3$;
c. when ring A is a 5-membered heteroaryl, then ring B is not phenyl optionally substituted with one to two groups independently selected from F, Cl, $SO_2CH_3$, $C(O)OCH_3$, methyl, ethyl, t-butyl, methoxy, ethoxy, O-phenyl, $CF_3$, OH, and $NO_2$;
d. when ring A is a 2,4-di-substituted 5-thiazolyl, then ring B is not substituted phenyl;
e. the compound is not:
  (1) $N^2$-2-pyridinyl-6-(3-pyridinyl)-1,3,5-triazine-2,4-diamine;
  (2) 6-(6-methoxy-3-pyridinyl)-$N^2$-(4-methylphenyl)-1,3,5-triazine-2,4-diamine;
  (3) 6-(2-methoxy-3-pyridinyl)-$N^2$-(4-methylphenyl)-1,3,5-triazine-2,4-diamine;
  (4) $N^2$-(3-chlorophenyl)-6-(2-chloro-4-pyridinyl)-1,3,5-triazine-2,4-diamine;
  (5) 3-[[4-[4-amino-6-[(3-chlorophenyl)amino]-1,3,5-triazin-2-yl]-2-pyridinyl]amino]-1-propanol;
  (6) N-[3-[[4-amino-6-(2-methyl-4-pyrimidinyl)-1,3,5-triazin-2-yl]amino]-4-methylphenyl]-N'-[4-chloro-3-(trifluoromethyl)phenyl]-urea;
  (7) $N^4,N^{4'}$-diphenyl-[2,2'-bi-1,3,5-triazine]-4,4',6,6'-tetramine;
  (8) 6,6'-(2,6-pyridinediyl)bis[N-phenyl-1,3,5-triazine-2,4-diamine; or
  (9) 6,6'-(2,3-pyrazinediyl)bis[N-phenyl-1,3,5-triazine-2,4-diamine.

The compound of Formula I or II or as described in any one of the embodiments herein inhibits mutant IDH2, particularly mutant IDH2 having alpha hydroxyl neoactivity. Also described herein are pharmaceutical compositions comprising a compound of Formula I and methods of using such compositions to treat cancers characterized by the presence of a mutant IDH2.

DETAILED DESCRIPTION

The details of construction and the arrangement of components set forth in the following description or illustrated in the drawings are not meant to be limiting. Other embodiments and different ways to practice the invention are expressly included. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

DEFINITIONS

The term "halo" or "halogen" refers to any radical of fluorine, chlorine, bromine or iodine.

The term "alkyl" refers to a fully saturated or unsaturated hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups. The term "alkyl" includes "alkenyl" and "alkynyl".

The term "alkylene" refers to a divalent alkyl, e.g., —$CH_2$—, —$CH_2CH_2$—, —$CH_2CH_2CH_2$— and —$CH_2CH(CH_3)CH_2$—.

The term "alkenyl" refers to a straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent.

The term "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The term "alkoxy" refers to an —O-alkyl radical. The term "haloalkoxy" refers to an alkoxy in which one or more hydrogen atoms are replaced by halo, and includes alkoxy moieties in which all hydrogens have been replaced by halo (e.g., perfluoroalkoxy).

Unless otherwise specified, the term "aryl" refers to a fully aromatic monocyclic, bicyclic, or tricyclic hydrocarbon ring system. Examples of aryl moieties are phenyl, naphthyl, and anthracenyl. Unless otherwise specified, any ring atom in an aryl can be substituted by one or more substituents. The term "monocyclic aryl" means a monocyclic fully romatic hydrocarbon ring system, optionally substituted by one or more substituents which can not form a fused bicyclic or tricyclic ring.

The term "carbocyclyl" refers to a non-aromatic, monocyclic, bicyclic, or tricyclic hydrocarbon ring system. Carbocyclyl groups include fully saturated ring systems (e.g., cycloalkyls), and partially saturated ring systems.

The term "cycloalkyl" as employed herein includes saturated cyclic, bicyclic, tricyclic, or polycyclic hydrocarbon groups having 3 to 12 carbons. Any ring atom can be substituted (e.g., by one or more substituents). Examples of cycloalkyl moieties include, but are not limited to, cyclopropyl, cyclohexyl, methylcyclohexyl, adamantyl, and norbornyl.

Unless otherwise specified, the term "heteroaryl" refers to a fully aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (or the oxidized forms such as $N^+$—$O^-$, S(O) and $S(O)_2$). The term "monocyclic heteroaryl" means a monocyclic fully romatic ring system having 1-3 heteroatoms, optionally substituted by one or more substituents which can not form a fused bicyclic or tricyclic ring.

The term "heterocyclyl" refers to a nonaromatic, 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (or the oxidized forms such as $N^+$—$O^-$, S(O) and $S(O)_2$). The heteroatom may optionally be the point of attachment of the heterocyclyl substituent. Examples of heterocyclyl include, but are not limited to, tetrahydrofuranyl, tetrahydropyranyl, piperidinyl, morpholino, pyrrolinyl, pyrimidinyl, and pyrrolidinyl. Heterocyclyl groups include fully saturated ring systems, and partially saturated ring systems.

Bicyclic and tricyclic ring systems containing one or more heteroatoms and both aromatic and non-aromatic rings are considered to be heterocyclyl or heteroaryl groups. Bicyclic or tricyclic ring systems where an aryl or a heteroaryl is fused to a carbocyclyl or heterocyclyl and the point of attachment from the ring system to the rest of the molecule is through an aromatic ring are considered to be aryl or heteroaryl groups, respectively. Bicyclic or tricyclic ring systems where an aryl or a heteroaryl is fused to a carbocyclyl or heterocyclyl and the point of attachment from the ring system to the rest of the molecule is through the non-aromatic ring are considered to be carbocyclyl (e.g., cycloalkyl) or heterocyclyl groups, respectively.

Aryl, heteroaryl, carbocyclyl (including cycloalkyl), and heterocyclyl groups, either alone or a part of a group (e.g., the aryl portion of an aralkyl group), are optionally substituted at one or more substitutable atoms with, unless specified otherwise, substituents independently selected from: halo, —C≡N, $C_1$-$C_4$ alkyl, =O, —$OR^b$, —$OR^{b'}$, —$SR^b$, —$SR^{b'}$, —($C_1$-$C_4$ alkyl)-N($R^b$)($R^b$), —($C_1$-$C_4$ alkyl)-N($R^b$)($R^{b'}$), —N($R^b$)($R^b$), —N($R^b$)($R^{b'}$), —O—($C_1$-$C_4$ alkyl)-N($R^b$)($R^b$), —O—($C_1$-$C_4$ alkyl)-N($R^b$)($R^{b'}$), —($C_1$-$C_4$ alkyl)-O—($C_1$-$C_4$ alkyl)-N($R^b$)($R^b$), —($C_1$-$C_4$ alkyl)-O—($C_1$-$C_4$ alkyl)-N($R^b$)($R^{b'}$), —C(O)—N($R^b$)($R^b$), —($C_1$-$C_4$ alkyl)-C(O)—N($R^b$)($R^b$), —($C_1$-$C_4$ alkyl)-C(O)—N($R^b$)($R^{b'}$), —$OR^{b'}$, $R^{b'}$, —C(O)($C_1$-$C_4$ alkyl), —C(O)$R^{b'}$, —C(O)N($R^{b'}$)($R^b$), —N($R^b$)C(O)($R^b$), —N($R^b$)C(O)($R^{b'}$), —N($R^b$)$SO_2$($R^b$), —$SO_2$N($R^b$)($R^b$), —N($R^b$)$SO_2$($R^{b'}$), and —$SO_2$N($R^b$)($R^{b'}$), wherein any alkyl substituent is optionally further substituted with one or more of —OH, —O—($C_1$-$C_4$ alkyl), halo, —$NH_2$, —NH($C_1$-$C_4$ alkyl), or —N($C_1$-$C_4$ alkyl)$_2$;

each $R^b$ is independently selected from hydrogen, and —$C_1$-$C_4$ alkyl; or two $R^b$s are taken together with the nitrogen atom to which they are bound to form a 4- to 8-membered heterocyclyl optionally comprising one additional heteroatom selected from N, S, and O; and each $R^{b'}$ is independently selected from $C_3$-$C_7$ carbocyclyl, phenyl, heteroaryl, and heterocyclyl, wherein one or more substitutable positions on said phenyl, cycloalkyl, heteroaryl or heterocycle substituent is optionally further substituted with one or more of —($C_1$-$C_4$ alkyl), —($C_1$-$C_4$ fluoroalkyl), —OH, —O—($C_1$-$C_4$ alkyl), —O—($C_1$-$C_4$ fluoroalkyl), halo, —$NH_2$, —NH($C_1$-$C_4$ alkyl), or —N($C_1$-$C_4$ alkyl)$_2$.

Heterocyclyl groups, either alone or as part of a group, are optionally substituted on one or more any substitutable nitrogen atom with oxo, —$C_1$-$C_4$ alkyl, or fluoro-substituted $C_1$-$C_4$ alkyl.

The term "substituted" refers to the replacement of a hydrogen atom by another group.

As used herein, the term "elevated levels of 2HG" means 10%, 20% 30%, 50%, 75%, 100%, 200%, 500% or more 2HG then is present in a subject that does not carry a mutant IDH2 allele. The term "elevated levels of 2HG" may refer to the amount of 2HG within a cell, within a tumor, within an organ comprising a tumor, or within a bodily fluid.

The term "bodily fluid" includes one or more of amniotic fluid surrounding a fetus, aqueous humour, blood (e.g., blood plasma), serum, Cerebrospinal fluid, cerumen, chyme, Cowper's fluid, female ejaculate, interstitial fluid, lymph, breast milk, mucus (e.g., nasal drainage or phlegm), pleural fluid, pus, saliva, sebum, semen, serum, sweat, tears, urine, vaginal secretion, or vomit.

As used herein, the terms "inhibit" or "prevent" include both complete and partial inhibition and prevention. An inhibitor may completely or partially inhibit the intended target.

The term "treat" means decrease, suppress, attenuate, diminish, arrest, or stabilize the development or progression of a disease/disorder (e.g., a cancer), lessen the severity of the disease/disorder (e.g., a cancer) or improve the symptoms associated with the disease/disorder (e.g., a cancer).

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, the term "subject" is intended to include human and non-human animals. Exemplary human subjects include a human patient (referred to as a patient) having a disorder, e.g., a disorder described herein or a normal subject. The term "non-human animals" of one aspect of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Compounds

Provided is a compound of Structural Formula I, or a pharmaceutically acceptable salt or hydrate thereof:

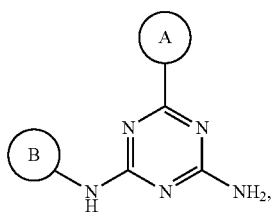

(I)

wherein:
ring A is an optionally substituted 5-6 member monocyclic aryl or monocyclic heteroaryl; and
ring B is an optionally substituted 5-6 member monocyclic aryl or monocyclic heteroaryl; wherein:
a. ring A and ring B are not both an optionally substituted 6 member monocyclic aryl;

b. when ring A is unsubstituted pyridyl, then ring B is not phenyl optionally substituted with one to three groups independently selected from methyl, ethyl, t-butyl, methoxy, CH(OH)CH$_3$, Cl, Br, SH, and CF$_3$;

c. when ring A is a 5-membered heteroaryl, then ring B is not phenyl optionally substituted with one to two groups independently selected from F, Cl, SO$_2$CH$_3$, C(O)OCH$_3$, methyl, ethyl, t-butyl, methoxy, ethoxy, O-phenyl, CF$_3$, OH, and NO$_2$;

d. when ring A is a 2,4-di-substituted 5-thiazolyl, then ring B is not substituted phenyl;

e. the compound is not:
(1) $N^2$-2-pyridinyl-6-(3-pyridinyl)-1,3,5-triazine-2,4-diamine;
(2) 6-(6-methoxy-3-pyridinyl)-$N^2$-(4-methylphenyl)-1,3,5-triazine-2,4-diamine;
(3) 6-(2-methoxy-3-pyridinyl)-$N^2$-(4-methylphenyl)-1,3,5-triazine-2,4-diamine;
(4) $N^2$-(3-chlorophenyl)-6-(2-chloro-4-pyridinyl)-1,3,5-triazine-2,4-diamine;
(5) 3-[[4-[4-amino-6-[(3-chlorophenyl)amino]-1,3,5-triazin-2-yl]-2-pyridinyl]amino]-1-propanol;
(6) N-[3-[[4-amino-6-(2-methyl-4-pyrimidinyl)-1,3,5-triazin-2-yl]amino]-4-methylphenyl]-N'-[4-chloro-3-(trifluoromethyl)phenyl]-urea;
(7) $N^4,N^{4'}$-diphenyl-[2,2'-bi-1,3,5-triazine]-4,4',6,6'-tetramine;
(8) 6,6'-(2,6-pyridinediyl)bis[N-phenyl-1,3,5-triazine-2,4-diamine; or
(9) 6,6'-(2,3-pyrazinediyl)bis[N-phenyl-1,3,5-triazine-2,4-diamine.

In some embodiments, ring A is an optionally substituted 6-membered monocyclic aryl. In some embodiments, ring A is an optionally substituted 5-6 membered heteroaryl. In some embodiments, ring A is an optionally substituted 6 membered heteroaryl.

In some embodiments, ring A is selected from phenyl, pyrazolyl, oxazolyl, isoxazolyl, pyridinyl, pyrimidinyl, pyrazinyl, and thiazolyl, wherein ring A is optionally substituted with up to two substituents independently selected from halo, —$C_1$-$C_4$ alkyl, —$C_1$-$C_4$ haloalkyl, —$C_1$-$C_4$ hydroxyalkyl, —NH—S(O)$_2$—($C_1$-$C_4$ alkyl), —S(O)$_2$NH($C_1$-$C_4$ alkyl), —CN, —S(O)$_2$—($C_1$-$C_4$ alkyl), $C_1$-$C_4$ alkoxy, —NH($C_1$-$C_4$ alkyl), —OH, —OCF$_3$, —CN, —NH$_2$, —C(O)NH$_2$, —C(O)NH($C_1$-$C_4$ alkyl), —C(O)—N($C_1$-$C_4$ alkyl)$_2$, and cyclopropyl optionally substituted with OH.

In some embodiments, ring A is selected from phenyl, pyrazolyl, oxazolyl, isoxazolyl, pyridinyl, pyrimidinyl, pyrazinyl, and thiazolyl, wherein ring A is optionally substituted with up to two substituents independently selected from halo, —$C_1$-$C_4$ alkyl, —$C_1$-$C_4$ haloalkyl, —$C_1$-$C_4$ hydroxyalkyl, —NH—S(O)$_2$—($C_1$-$C_4$ alkyl), —S(O)$_2$NH($C_1$-$C_4$ alkyl), —CN, —S(O)$_2$—($C_1$-$C_4$ alkyl), $C_1$-$C_4$ alkoxy, —NH($C_1$-$C_4$ alkyl), —OH, —CN, and —NH$_2$.

In some embodiments, ring B is selected from phenyl, pyrazolyl, oxazolyl, isoxazolyl, thiazolyl, pyridinyl, pyrimidinyl, pyridazinyl, and pyrazinyl, wherein ring B is optionally substituted with up to two substituents independently selected from halo, —$C_1$-$C_4$ alkyl, —$C_2$-$C_4$ alkynyl, —$C_1$-$C_4$ haloalkyl, —$C_1$-$C_4$ hydroxyalkyl, $C_3$-$C_6$ cycloalkyl, —($C_0$-$C_2$ alkylene)-O—$C_1$-$C_4$ alkyl, —O—($C_1$-$C_4$ alkylene)-$C_3$-$C_6$ cycloalkyl, —NH—S(O)$_2$—($C_1$-$C_4$ alkyl), —S(O)$_2$NH($C_1$-$C_4$ alkyl), —S(O)$_2$—NH—($C_3$-$C_6$ cycloalkyl), —S(O)$_2$-(saturated heterocyclyl), —CN, —S(O)$_2$—($C_1$-$C_4$ alkyl), —NH($C_1$-$C_4$ alkyl), —N($C_1$-$C_4$ alkyl)$_2$, —OH, C(O)—O—($C_1$-$C_4$ alkyl), saturated heterocyclyl, and —NH$_2$.

In another embodiment, the compound is a compound having Structural Formula II:

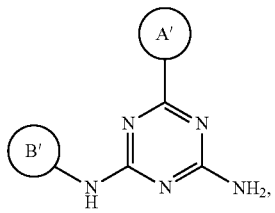

(II)

or a pharmaceutically acceptable salt thereof, wherein:

ring A' is selected from phenyl, pyrimidin-2-yl, pyrimidin-4-yl, pyrimidin-5-yl, oxazol-4-yl, isoxazol-3-yl, thiazol-2-yl, pyridin-3-yl and pyridin-2-yl, wherein ring A' is optionally substituted with one or two substituents independently selected from 1-propenyl, -cyclopropyl-OH, chloro, fluoro, —$CF_3$, —$CHF_2$, —$CH_3$, —$CH_2CH_3$, —$CF_2CH_3$, —S(O)$CH_3$, —S(O)$_2CH_3$, —$CH_2OH$, —CH(OH)$CH_3$, —CH(OH)$CF_3$, —OH, —$OCH_3$, —$OCF_3$, —$OCH_2CH_3$, —C(O)—$NH_2$, —$CH_2NH_2$, —$NH_2$, —NH($CH_3$), —CN and —N($CH_3$)$_2$; and ring B' is selected from phenyl, pyridin-3-yl, pyridin-4-yl, pyridazin-4-yl, isoxazol-4-yl, isoxazol-3-yl, thiazol-5-yl, pyrimidin-5-yl and pyrazol-4-yl, wherein ring B' is optionally substituted with one to two substituents independently selected from halo; —CN; —OH; $C_1$-$C_4$ alkyl optionally substituted with halo, CN or —OH; —S(O)$_2$—$C_1$-$C_4$ alkyl; —S(O)—$C_1$-$C_4$ alkyl; —S(O)$_2$—NH—$C_1$-$C_4$ alkyl; —S(O)$_2$—NH—$CH_2$—$CF_3$; —S(O)$_2$—N($C_1$-$C_4$ alkyl)$_2$; —S(O)$_2$-azetidin-1-yl; —O—$C_1$-$C_4$ alkyl; —$CH_2$—O—$CH_3$, morpholin-4-yl, cyclopropyl, cyclopropyl-$C_1$-$C_4$ alkyl, cyclopropyl-$C_1$-$C_4$ alkoxy, cyclopropyl-CN, —S(O)$_2$—NH-cyclopropyl; —S(O)$_2$—NH—$CH_2$-cyclopropyl; —C(O)—$C_1$-$C_4$ alkyl, —C(O)—O—$CH_3$; wherein:

a. ring A' and ring B' are not both an optionally substituted 6 member monocyclic aryl;
b. when ring A' is unsubstituted pyridyl, then ring B' is not phenyl optionally substituted with one to three groups independently selected from methyl, ethyl, t-butyl, methoxy, CH(OH)$CH_3$, Cl, Br, SH, and $CF_3$;
c. when ring A' is a 5-membered heteroaryl, then ring B' is not phenyl optionally substituted with one to two groups independently selected from F, Cl, SO$_2CH_3$, C(O)O$CH_3$, methyl, ethyl, t-butyl, methoxy, ethoxy, O-phenyl, $CF_3$, OH, and $NO_2$;
d. the compound is not:
  (1) $N^2$-2-pyridinyl-6-(3-pyridinyl)-1,3,5-triazine-2,4-diamine;
  (2) 6-(6-methoxy-3-pyridinyl)-$N^2$-(4-methylphenyl)-1,3,5-triazine-2,4-diamine;
  (3) 6-(2-methoxy-3-pyridinyl)-$N^2$-(4-methylphenyl)-1,3,5-triazine-2,4-diamine;
  (4) $N^2$-(3-chlorophenyl)-6-(2-chloro-4-pyridinyl)-1,3,5-triazine-2,4-diamine;
  (5) 3-[[4-[4-amino-6-[(3-chlorophenyl)amino]-1,3,5-triazin-2-yl]-2-pyridinyl]amino]-1-propanol;
  (6) N-[3-[[4-amino-6-(2-methyl-4-pyrimidinyl)-1,3,5-triazin-2-yl]amino]-4-methylphenyl]-N'-[4-chloro-3-(trifluoromethyl)phenyl]-urea;
  (7) $N^4$,$N^{4'}$-diphenyl-[2,2'-bi-1,3,5-triazine]-4,4',6,6'-tetramine;
  (8) 6,6'-(2,6-pyridinediyl)bis[N-phenyl-1,3,5-triazine-2,4-diamine; or
  (9) 6,6'-(2,3-pyrazinediyl)bis[N-phenyl-1,3,5-triazine-2,4-diamine.

In certain embodiments of Formula II, ring A' is selected from 2-chlorophenyl, 2-fluorophenyl, 2-methoxyphenyl, 3-hydroxyphenyl, 3-amidophenyl, 3-methylsulfinylphenyl, 3-methylsulfonylphenyl, 3-(1-methanol)phenyl, 3-methanaminephenyl, 3-methoxy-2-fluorophenyl, 5-methoxy-2-fluorophenyl, 3-hydroxy-2-fluorophenyl, 5-hydroxy-2-fluorophenyl, 5-hydroxy-3-fluorophenyl, 3-methanolphenyl, 3,5-dihydroxyphenyl, 3-trifluoromethyl-5-chlorophenyl, 3-(1-hydoxy-2,2,2-trifluoroethyl)phenyl, 3-(1-hydoxyethyl)phenyl, 3-(1-hydoxycyclopropyl)phenyl, 3-hydroxymethyl-5-phenol, pyridin-2-yl, 3-fluoropyridin-2-yl, 3-cyanopyridin-2-yl, 3,6-difluoropyridin-2-yl, 3-fluoro-6-methoxypyridin-2-yl, 3-fluoro-6-hydroxypyridin-2-yl, 3-fluoro-6-aminopyridin-2-yl, 4-fluoro-6-aminopyridin-2-yl, 6-propen-1-ylpyridin-2-yl, 6-prop-1-ylpyridin-2-yl, 6-methylaminopyridin-2-yl, 3-fluoro-6-trifluoromethylpyridin-2-yl, 4-chloro-6-aminopyridin-2-yl, 4-fluoro-6-aminopyridin-2-yl, 4-chloro-6-methoxypyridin-2-yl, 6-aminopyridin-3-yl, 2-methoxypyridin-3-yl, 6-aminopyridin-2-yl, 6-chloropyridin-2-yl, 6-trifluoromethylpyridin-2-yl, 6-difluoromethylpyridin-2-yl, 4-(CH$_2$OH)-6-trifluoromethylpyridin-2-yl, 4-(CH$_2$OH)-6-chloro-pyridin-2-yl, 6-(1,1-difluoroethyl)-4-fluoropyridin-2-yl, 4-trifluoromethylpyrimidin-2-yl, 4-aminopyrimidin-2-yl, 6-trifluoromethyl-4-aminopyrimidin-2-yl, 4-trifluoromethyl-6-aminopyrimidin-2-yl, 4-aminopyrimidin-2-yl, 2-aminopyrimidin-4-yl, 2-aminopyrimidin-5-yl, 4,6-dichloropyridin-2-yl, 3,5-dichlorophenyl, 2,6-difluorophenyl, 2-methyloxazol-4-yl, 3-methylisoxazol-5-yl, 4-trifluoromethyl-thiazol-2-yl, 4-methylthiazol-2-yl and phenyl.

In certain embodiments of Formula II, ring B' is selected from 2-(morpholin-4-yl)pyridin-4-yl, 2-dimethylaminopyridin-4-yl, 3-(2-methyoxyethyl)phenyl, 3,5-difluorophenyl, 3-chlorophenyl, 3-cyanomethylphenyl, 3-cyanophenyl, 3-(cyclopropylmethyl)phenyl, 3-cyclopropylaminosulfonylphenyl, 3-cyclopropylaminosulfonylphenyl, 3-dimethylaminosulfonylphenyl, 3-ethylsulfonylphenyl, 3-fluorophenyl, 3-methylsulfonylphenyl, 4-fluorophenyl, 3-(1-hydroxyisopropyl)phenyl, 3-methylsulfonyl-5-chlorophenyl, 3-methylsulfonyl-5-fluorophenyl, 3-(N-2,2,2,-trifluoroethylaminosulfonyl)phenyl, 3-(N-cyclopropyl)benzamide, 5-chloropyridin-3-yl, 5-cyanopyridin-3-yl, 5-cyanopyridin-3-yl, 5-cyanopyridin-4-yl, 5-fluoropyridin-3-yl, 2-(1-hydroxyisopropyl)pyridin-4-yl, 5-trifluoromethypyridin-3-yl, 2-trifluoromethylpyridin-4-yl, 2-difluoromethylpyridin-4-yl, 2-chloropyridin-4-yl, 6-chloropyridin-4-yl, 6-cyanopyridin-4-yl, 2-cyanopyridin-4-yl, 6-cyclopropylpyridin-4-yl, 6-ethoxypyridin-4-yl, 6-fluoropyridin-3-yl, 2-fluoropyridin-4-yl, 5,6-difluoropyridin-3-yl, 6-fluoropyridin-4-yl, 6-methylpyridin-4-yl, 2-difluoromethylpyridin-4-yl, 6-trifluoromethylpyridin-4-yl, 2-(1-methoxycyclopropyl)pyridin-4-yl, 2-cyclopropylpyridin-4-yl, 2-(propan-1-one)pyridin-4-yl, 2-(1-methylcyclopropyl)pyridin-4-yl, 2-(1-cyanocyclopropyl)pyridin-4-yl, 2-(1-cyanoisopropyl)pyridin-4-yl, isoxazol-4-yl, phenyl, pyridin-4-yl, picolinat-2-yl, pyrimidin-5-yl, 1-propylpyrazol-4-yl, 6-methylpyridazin-4-yl, and thiazol-5-yl.

Further embodiments provided herein include combinations of one or more of the particular embodiments set forth above.

In another embodiment, the compound is selected from any one of the compounds set forth in Table 1, below.

TABLE 1

Representative Compounds

| Cmpd No | Structure |
|---|---|
| 114 | 6-(pyridin-3-yl)-N2-phenyl-1,3,5-triazine-2,4-diamine |
| 129 | 6-phenyl-N2-(pyridin-4-yl)-1,3,5-triazine-2,4-diamine |
| 147 | 6-phenyl-N2-(2-methylphenyl)-1,3,5-triazine-2,4-diamine |
| 154 | 6-phenyl-N2-(pyridin-3-yl)-1,3,5-triazine-2,4-diamine |
| 155 | 6-phenyl-N2-(pyridin-2-yl)-1,3,5-triazine-2,4-diamine |
| 156 | 6-(pyridin-4-yl)-N2-phenyl-1,3,5-triazine-2,4-diamine |

TABLE 1-continued

Representative Compounds

| Cmpd No | Structure |
|---|---|
| 169 | 6-phenyl-N2-(isoxazol-3-yl)-1,3,5-triazine-2,4-diamine |
| 184 | 6-(3-fluorophenyl)-N2-(pyridin-4-yl)-1,3,5-triazine-2,4-diamine |
| 185 | 6-(3-chlorophenyl)-N2-(pyridin-4-yl)-1,3,5-triazine-2,4-diamine |
| 193 | 6-phenyl-N2-(5-fluoropyridin-3-yl)-1,3,5-triazine-2,4-diamine |
| 196 | 6-phenyl-N2-(6-fluoropyridin-3-yl)-1,3,5-triazine-2,4-diamine |
| 197 | 6-phenyl-N2-(2-cyanopyridin-4-yl)-1,3,5-triazine-2,4-diamine |

TABLE 1-continued
Representative Compounds
| Cmpd No | Structure |
|---|---|
| 199 | 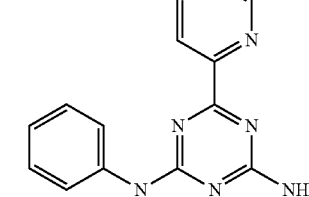 |
| 200 | 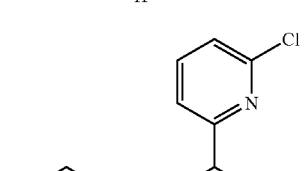 |
| 202 | 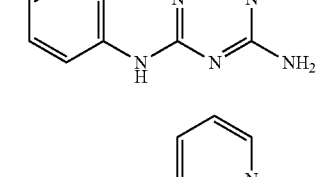 |
| 224 | 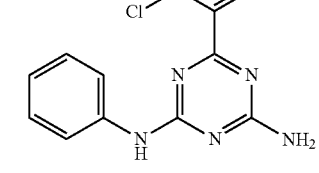 |
| 226 | 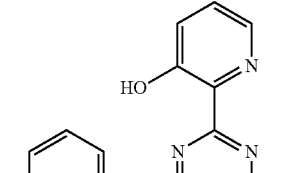 |
| 227 | 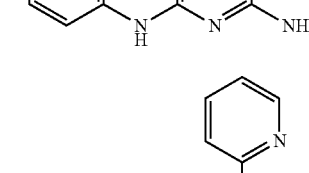 |
| 228 | |
| 229 | |
| 230 | |
| 231 | |
| 246 | |
| 247 | |

TABLE 1-continued

Representative Compounds

| Cmpd No | Structure |
|---|---|
| 266 | 6-phenyl-N2-(pyrimidin-5-yl)-1,3,5-triazine-2,4-diamine |
| 270 | 6-(4-(trifluoromethyl)pyridin-2-yl)-N2-phenyl-1,3,5-triazine-2,4-diamine |
| 281 | N2-(6-methylpyridin-3-yl)-6-phenyl-1,3,5-triazine-2,4-diamine |
| 288 | N2-(2-methylpyridin-4-yl)-6-phenyl-1,3,5-triazine-2,4-diamine |
| 289 | N2-(6-chloropyridin-3-yl)-6-phenyl-1,3,5-triazine-2,4-diamine |
| 290 | 6-(6-aminopyridin-2-yl)-N2-phenyl-1,3,5-triazine-2,4-diamine |
| 292 | N2-(5-fluoropyridin-4-yl)-6-phenyl-1,3,5-triazine-2,4-diamine |
| 293 | N2-(2-(dimethylamino)pyridin-4-yl)-6-phenyl-1,3,5-triazine-2,4-diamine |
| 298 | N2-(2-morpholinopyridin-4-yl)-6-phenyl-1,3,5-triazine-2,4-diamine |
| 299 | N2-(2-(azetidin-1-yl)pyridin-4-yl)-6-phenyl-1,3,5-triazine-2,4-diamine |
| 301 | N2-(2-(isopropylamino)pyridin-4-yl)-6-phenyl-1,3,5-triazine-2,4-diamine |

TABLE 1-continued

Representative Compounds

| Cmpd No | Structure |
|---|---|
| 302 | 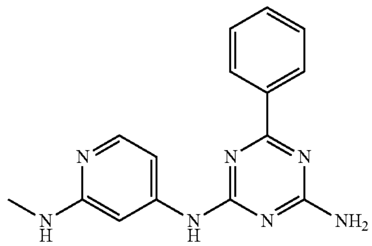 [SMILES: CNc1cc(Nc2nc(N)nc(-c3ccccc3)n2)ccn1] |
| 303 | 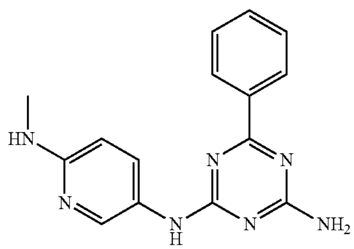 [SMILES: CNc1ccc(Nc2nc(N)nc(-c3ccccc3)n2)cn1] |
| 308 | 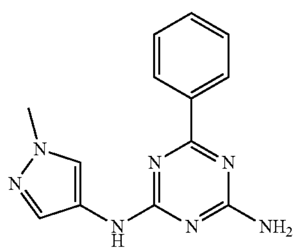 [SMILES: Cn1cc(Nc2nc(N)nc(-c3ccccc3)n2)cn1] |
| 309 | 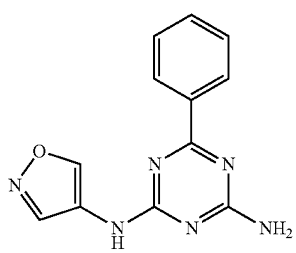 [SMILES: Nc1nc(Nc2cnoc2)nc(-c2ccccc2)n1] |
| 310 | 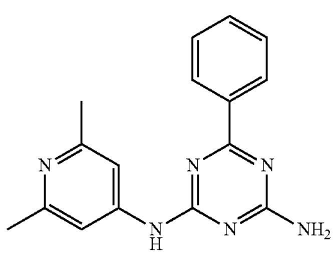 [SMILES: Cc1cc(Nc2nc(N)nc(-c3ccccc3)n2)cc(C)n1] |
| 311 | 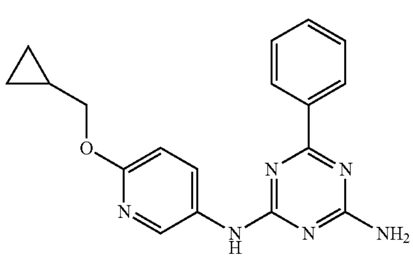 [SMILES: Nc1nc(Nc2ccc(OCC3CC3)nc2)nc(-c2ccccc2)n1] |
| 312 | |
| 313 | |
| 314 | |
| 315 | |
| 316 | |
| 318 | |

TABLE 1-continued

Representative Compounds

| Cmpd No | Structure |
|---------|-----------|
| 319 | 4-(2-fluorophenyl)-N-(2-(trifluoromethyl)pyridin-4-yl)-1,3,5-triazine-2,4-diamine |
| 320 | 4-(2-fluorophenyl)-N-(5-fluoropyridin-3-yl)-1,3,5-triazine-2,4-diamine |
| 321 | 5-((4-amino-6-(2-fluorophenyl)-1,3,5-triazin-2-yl)amino)nicotinonitrile |
| 322 | N-(5-fluoropyridin-3-yl)-6-(pyridin-2-yl)-1,3,5-triazine-2,4-diamine |
| 323 | 6-(6-chloropyridin-2-yl)-N-(5-fluoropyridin-3-yl)-1,3,5-triazine-2,4-diamine |
| 325 | 6-(6-chloropyridin-2-yl)-N-(6-fluoropyridin-3-yl)-1,3,5-triazine-2,4-diamine |
| 326 | 6-(6-chloropyridin-2-yl)-N-(3-(methylsulfonyl)phenyl)-1,3,5-triazine-2,4-diamine |
| 327 | 6-(3-aminophenyl)-N-(pyridin-4-yl)-1,3,5-triazine-2,4-diamine |
| 328 | 3-(4-amino-6-(pyridin-4-ylamino)-1,3,5-triazin-2-yl)phenol |
| 329 | 6-phenyl-N-(5-(trifluoromethyl)pyridin-3-yl)-1,3,5-triazine-2,4-diamine |
| 330 | N-(5-chloropyridin-3-yl)-6-(pyridin-2-yl)-1,3,5-triazine-2,4-diamine |
| 331 | N2-(6-(methylamino)pyridin-2-yl)-N4-phenyl-1,3,5-triazine-2,4,6-triamine |

TABLE 1-continued

Representative Compounds

| Cmpd No | Structure |
|---|---|
| 332 | (1-methylimidazol-4-yl)-NH-triazine(NH₂)-phenyl |
| 334 | (2-trifluoromethylpyridin-4-yl)-NH-triazine(NH₂)-(pyridin-2-yl) |
| 337 | (isoxazol-4-yl)-NH-triazine(NH₂)-(6-trifluoromethylpyridin-2-yl) |
| 340 | (3,5-difluorophenyl)-NH-triazine(NH₂)-(6-chloropyridin-2-yl) |
| 343 | (2-methylpyrimidin-5-yl)-NH-triazine(NH₂)-phenyl |
| 344 | (6-fluoropyridin-3-yl)-NH-triazine(NH₂)-(6-chloropyridin-2-yl) |
| 345 | (6-fluoropyridin-3-yl)-NH-triazine(NH₂)-(pyridin-2-yl) |
| 346 | (methyl pyridine-2-carboxylate-4-yl)-NH-triazine(NH₂)-phenyl |
| 350 | (2-methylpyridin-4-yl)-NH-triazine(NH₂)-phenyl |
| 353 | (pyrimidin-5-yl)-NH-triazine(NH₂)-(6-chloropyridin-2-yl) |
| 354 | (2-chloropyridin-4-yl)-NH-triazine(NH₂)-(6-chloropyridin-2-yl) |
| 355 | (2-cyanopyridin-4-yl)-NH-triazine(NH₂)-(6-chloropyridin-2-yl) |

TABLE 1-continued

Representative Compounds

| Cmpd No | Structure |
|---|---|
| 356 | 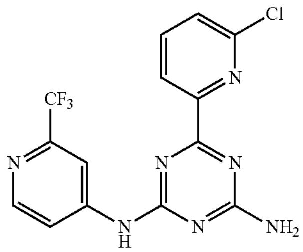 [SMILES: Nc1nc(Nc2ccnc(C(F)(F)F)c2)nc(-c2cccc(Cl)n2)n1] |
| 357 | 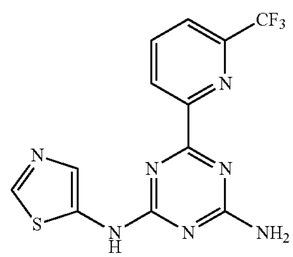 [SMILES: Nc1nc(Nc2cncs2)nc(-c2cccc(C(F)(F)F)n2)n1] |
| 358 | 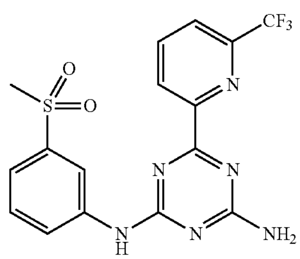 [SMILES: CS(=O)(=O)c1cccc(Nc2nc(N)nc(-c3cccc(C(F)(F)F)n3)n2)c1] |
| 359 | 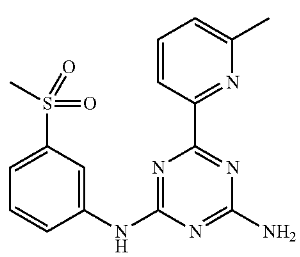 [SMILES: Cc1cccc(-c2nc(N)nc(Nc3cccc(S(C)(=O)=O)c3)n2)n1] |
| 360 | |аниц

TABLE 1-continued

Representative Compounds

| Cmpd No | Structure |
|---|---|
| 361 | 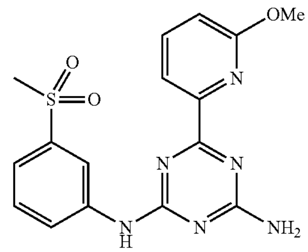 [SMILES: COc1cccc(-c2nc(N)nc(Nc3cccc(S(C)(=O)=O)c3)n2)n1] |
| 363 | 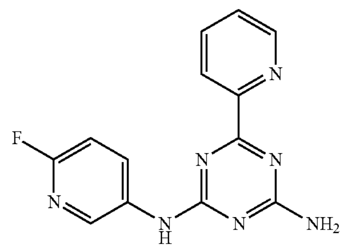 |
| 364 | 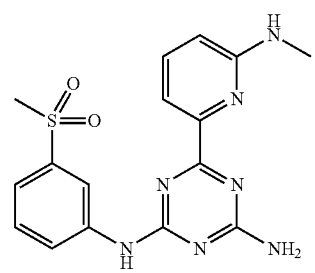 [SMILES: CNc1cccc(-c2nc(N)nc(Nc3cccc(S(C)(=O)=O)c3)n2)n1] |
| 365 | 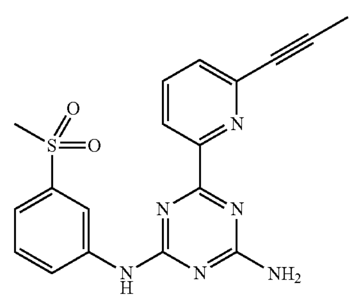 [SMILES: CC#Cc1cccc(-c2nc(N)nc(Nc3cccc(S(C)(=O)=O)c3)n2)n1] |
| 366 | 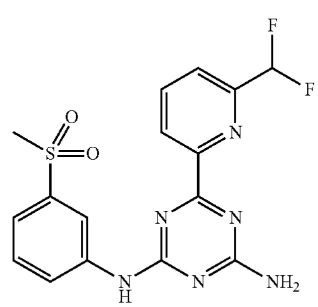 [SMILES: CS(=O)(=O)c1cccc(Nc2nc(N)nc(-c3cccc(C(F)F)n3)n2)c1] |

TABLE 1-continued

Representative Compounds

| Cmpd No | Structure |
|---|---|
| 367 | 4-(6-chloropyridin-2-yl)-N2-(5-(trifluoromethyl)pyridin-3-yl)-1,3,5-triazine-2,4-diamine |
| 368 | 4-(6-chloropyridin-2-yl)-N2-(2-fluoropyridin-4-yl)-1,3,5-triazine-2,4-diamine |
| 369 | 4-((4-amino-6-(2-fluorophenyl)-1,3,5-triazin-2-yl)amino)picolinonitrile |
| 371 | 4-(2-fluorophenyl)-N2-(2-fluoropyridin-4-yl)-1,3,5-triazine-2,4-diamine |
| 377 | N2-(2-fluoropyridin-4-yl)-4-(6-(trifluoromethyl)pyridin-2-yl)-1,3,5-triazine-2,4-diamine |
| 378 | 4-(6-(trifluoromethyl)pyridin-2-yl)-N2-(2-(trifluoromethyl)pyridin-4-yl)-1,3,5-triazine-2,4-diamine |
| 379 | 4-(6-(trifluoromethyl)pyridin-2-yl)-N2-(5-(trifluoromethyl)pyridin-3-yl)-1,3,5-triazine-2,4-diamine |
| 380 | N2-(6-fluoropyridin-3-yl)-4-(6-(trifluoromethyl)pyridin-2-yl)-1,3,5-triazine-2,4-diamine |
| 381 | N2-(5-fluoropyridin-3-yl)-4-(6-(trifluoromethyl)pyridin-2-yl)-1,3,5-triazine-2,4-diamine |
| 382 | 5-((4-amino-6-(6-chloropyridin-2-yl)-1,3,5-triazin-2-yl)amino)nicotinonitrile |
| 383 | 4-(6-chloropyridin-2-yl)-N2-(5-fluoropyridin-3-yl)-1,3,5-triazine-2,4-diamine |
| 386 | 4-(6-(trifluoromethyl)pyridin-2-yl)-N2-(5-(trifluoromethyl)pyridin-3-yl)-1,3,5-triazine-2,4-diamine |

Note: Structures shown are chemical diagrams; IUPAC names above are inferred for reference but the original table shows only drawn structures.

TABLE 1-continued

Representative Compounds

| Cmpd No | Structure |
|---|---|
| 387 | 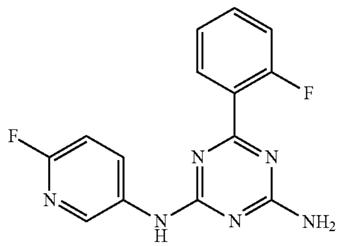 [SMILES: Nc1nc(Nc2ccc(F)nc2)nc(-c2ccccc2F)n1] |
| 388 | 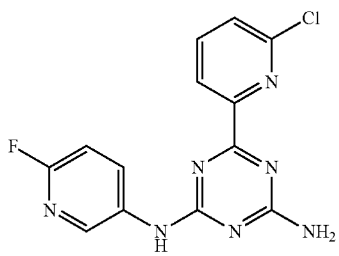 [SMILES: Nc1nc(Nc2ccc(F)nc2)nc(-c2cccc(Cl)n2)n1] |
| 389 | 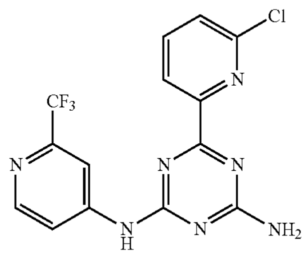 |
| 392 | 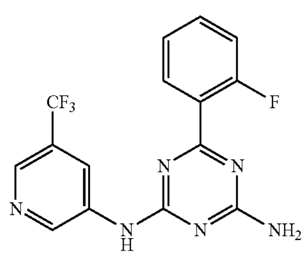 [SMILES: Nc1nc(Nc2cncc(C(F)(F)F)c2)nc(-c2ccccc2F)n1] |
| 393 | 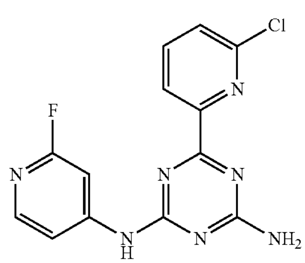 [SMILES: Nc1nc(Nc2ccnc(F)c2)nc(-c2cccc(Cl)n2)n1] |
| 395 | |
| 397 | |
| 398 | |
| 399 | |
| 400 | |

TABLE 1-continued

Representative Compounds

| Cmpd No | Structure |
|---|---|
| 401 | (structure) |
| 403 | (structure) |
| 410 | (structure) |
| 450 | (structure) |
| 454 | (structure) |
| 455 | (structure) |
| 456 | (structure) |
| 458 | (structure) |
| 459 | (structure) |
| 460 | (structure) |

TABLE 1-continued
Representative Compounds
| Cmpd No | Structure |
|---|---|
| 461 | 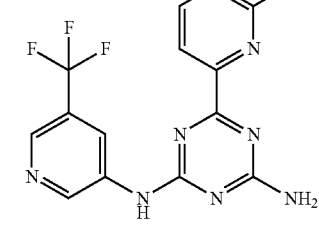 |
| 462 | 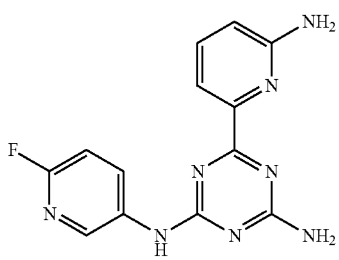 [SMILES: Nc1cccc(-c2nc(N)nc(Nc3ccc(F)nc3)n2)n1] |
| 463 | 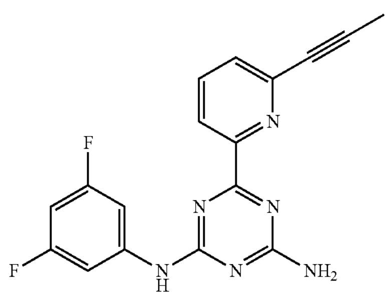 [SMILES: CC#Cc1cccc(-c2nc(N)nc(Nc3cc(F)cc(F)c3)n2)n1] |
| 464 | 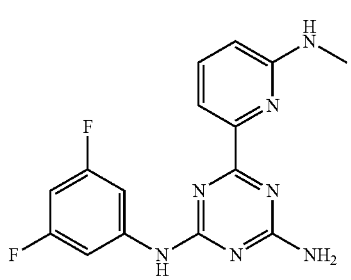 [SMILES: CNc1cccc(-c2nc(N)nc(Nc3cc(F)cc(F)c3)n2)n1] |
| 467 | 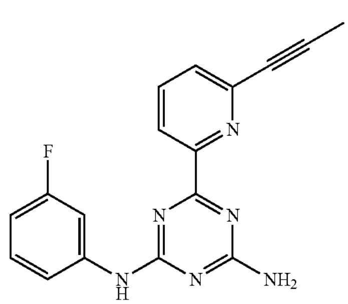 [SMILES: CC#Cc1cccc(-c2nc(N)nc(Nc3cccc(F)c3)n2)n1] |
| 468 | 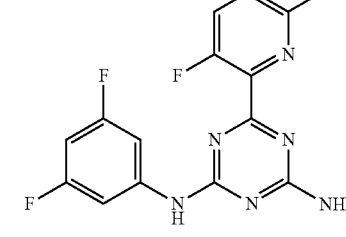 |
| 469 | |
| 470 | |
| 474 | |
| 477 | |

TABLE 1-continued

Representative Compounds

| Cmpd No | Structure |
|---|---|
| 481 | 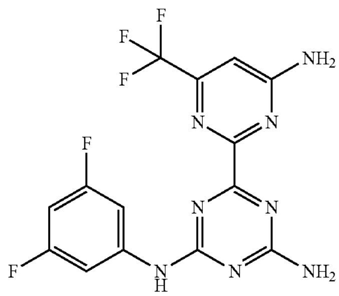 [SMILES: Nc1cc(C(F)(F)F)nc(-c2nc(N)nc(Nc3cc(F)cc(F)c3)n2)n1] |
| 482 | 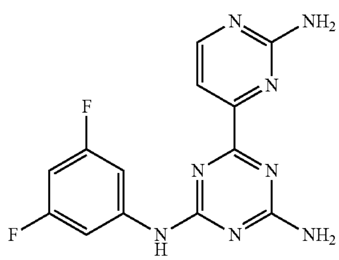 [SMILES: Nc1nccc(-c2nc(N)nc(Nc3cc(F)cc(F)c3)n2)n1] |
| 483 | 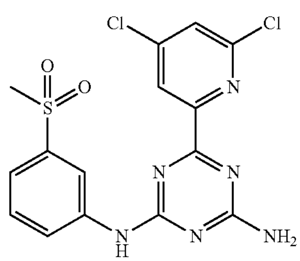 [SMILES: CS(=O)(=O)c1cccc(Nc2nc(N)nc(-c3cc(Cl)cc(Cl)n3)n2)c1] |
| 484 | 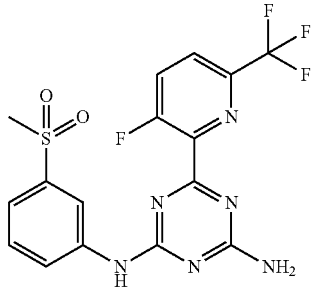 [SMILES: CS(=O)(=O)c1cccc(Nc2nc(N)nc(-c3nc(C(F)(F)F)ccc3F)n2)c1] |
| 485 | 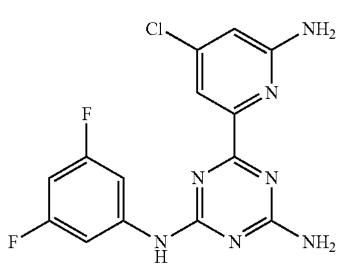 [SMILES: Nc1cc(Cl)cc(-c2nc(N)nc(Nc3cc(F)cc(F)c3)n2)n1] |
| 486 | |
| 487 | |
| 488 | |
| 489 | |
| 490 | |

TABLE 1-continued

Representative Compounds

| Cmpd No | Structure |
|---|---|
| 491 | (structure) |
| 492 | (structure) |
| 493 | (structure) |
| 494 | (structure) |
| 495 | (structure) |
| 496 | (structure) |
| 497 | (structure) |
| 498 | (structure) |
| 499 | (structure) |
| 500 | (structure) |

TABLE 1-continued
Representative Compounds
| Cmpd No | Structure |
|---|---|
| 501 | |
| 502 | |
| 503 | |
| 511 | |
| 514 | |
| 515 | 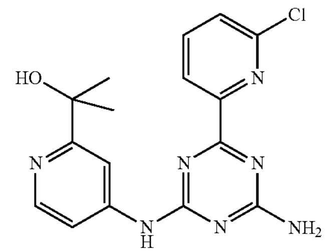 [SMILES: CC(C)(O)c1cc(Nc2nc(N)nc(-c3cccc(Cl)n3)n2)ccn1] |
| 516 | 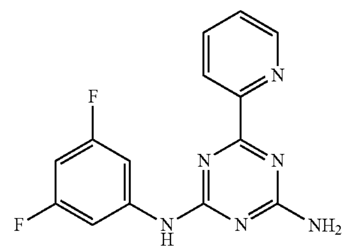 [SMILES: Nc1nc(Nc2cc(F)cc(F)c2)nc(-c2ccccn2)n1] |
| 518 | 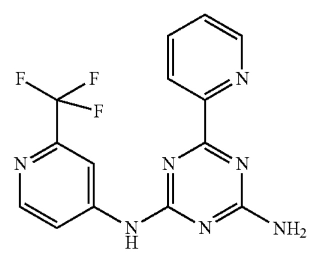 [SMILES: Nc1nc(Nc2ccnc(C(F)(F)F)c2)nc(-c2ccccn2)n1] |
| 519 | 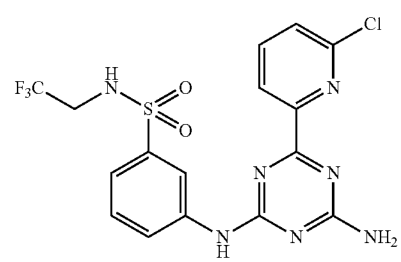 [SMILES: Nc1nc(Nc2cccc(S(=O)(=O)NCC(F)(F)F)c2)nc(-c2cccc(Cl)n2)n1] |
| 521 | 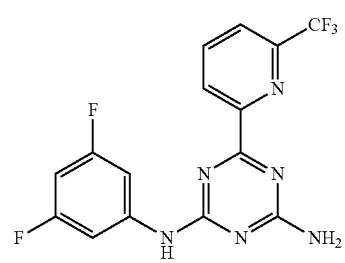 [SMILES: Nc1nc(Nc2cc(F)cc(F)c2)nc(-c2cccc(C(F)(F)F)n2)n1] |
| 522 | 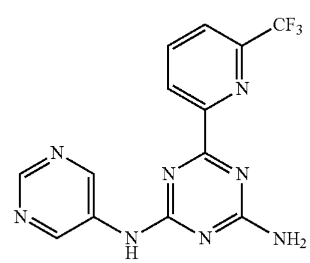 [SMILES: Nc1nc(Nc2cncnc2)nc(-c2cccc(C(F)(F)F)n2)n1] |
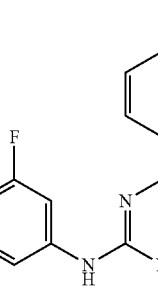

TABLE 1-continued
Representative Compounds
| Cmpd No | Structure |
|---|---|
| 528 | 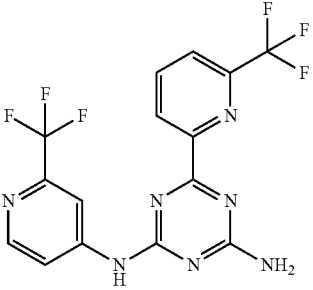 |
| 535 | 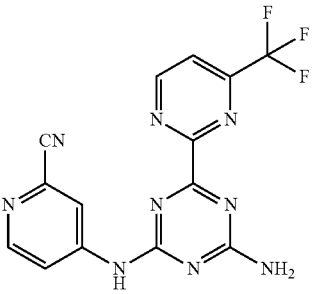 [SMILES: N#Cc1cc(Nc2nc(N)nc(-c3nccc(C(F)(F)F)n3)n2)ccn1] |
| 536 | 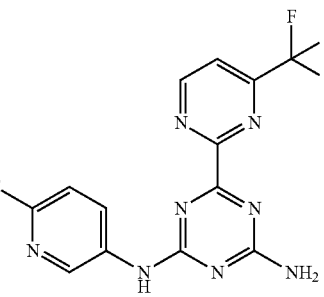 |
| 537 | 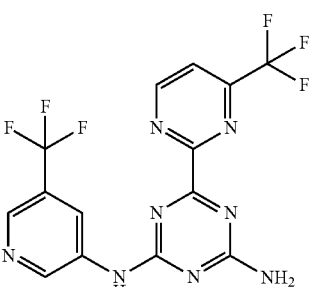 |
| 538 | 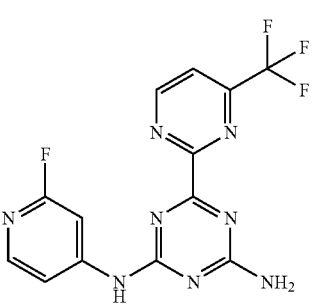 [SMILES: Nc1nc(Nc2ccnc(F)c2)nc(-c2nccc(C(F)(F)F)n2)n1] |
| 540 | 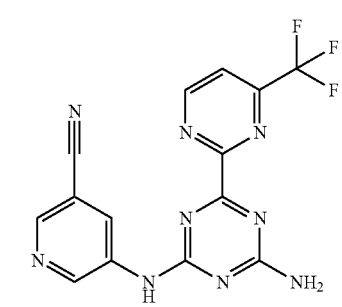 |
| 541 | 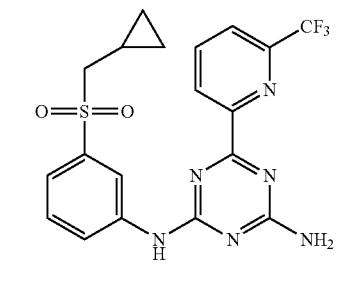 [SMILES: Nc1nc(Nc2cccc(S(=O)(=O)CC3CC3)c2)nc(-c2cccc(C(F)(F)F)n2)n1] |
| 543 | 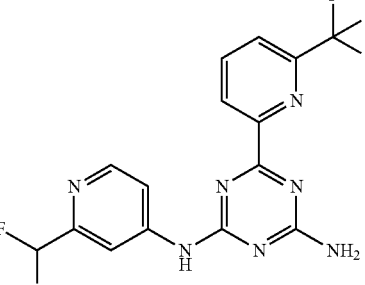 |
| 551 | 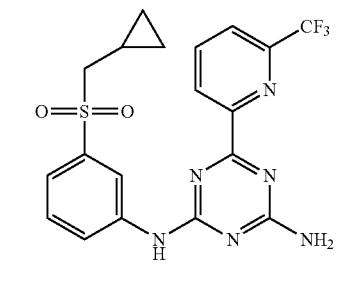 [SMILES: Nc1nc(Nc2cccc(S(=O)(=O)CC3CC3)c2)nc(-c2cccc(C(F)(F)F)n2)n1] |
| 554 | 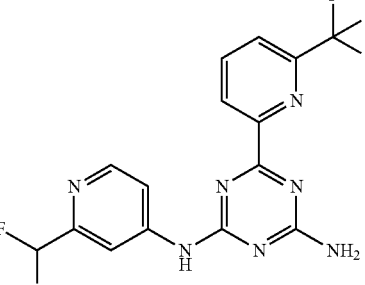 |

TABLE 1-continued

Representative Compounds

| Cmpd No | Structure |
|---|---|
| 555 | 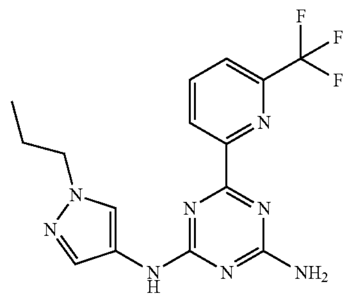 [SMILES: CCCn1cc(Nc2nc(N)nc(-c3cccc(C(F)(F)F)n3)n2)cn1] |
| 557 | 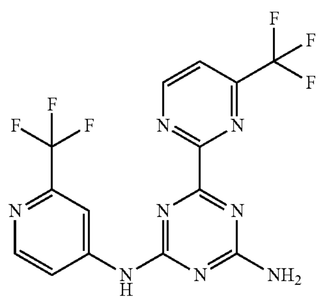 [SMILES: Nc1nc(Nc2ccnc(C(F)(F)F)c2)nc(-c2nccc(C(F)(F)F)n2)n1] |
| 559 | 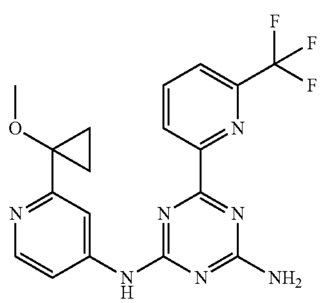 [SMILES: COC1(c2cc(Nc3nc(N)nc(-c4cccc(C(F)(F)F)n4)n3)ccn2)CC1] |
| 560 | 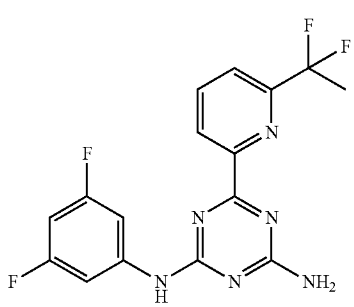 [SMILES: CC(F)(F)c1cccc(-c2nc(N)nc(Nc3cc(F)cc(F)c3)n2)n1] |
| 561 | 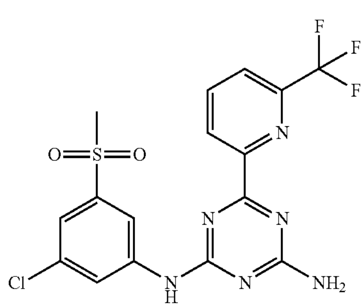 [SMILES: CS(=O)(=O)c1cc(Cl)cc(Nc2nc(N)nc(-c3cccc(C(F)(F)F)n3)n2)c1] |
| 563 | |
| 567 | |
| 570 | |
| 572 | |
| 574 | |

TABLE 1-continued

Representative Compounds

| Cmpd No | Structure |
|---------|-----------|
| 576 | 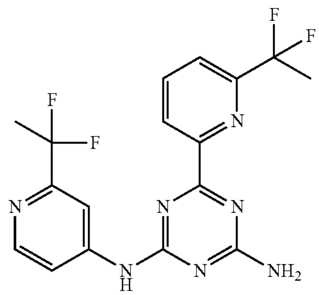 [SMILES: CC(F)(F)c1cc(Nc2nc(N)nc(-c3cccc(C(C)(F)F)n3)n2)ccn1] |
| 581 | 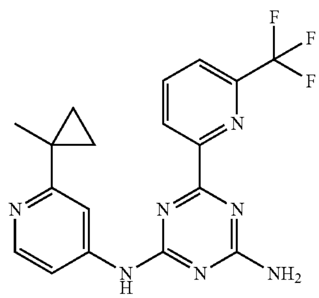 [SMILES: CC1(c2cc(Nc3nc(N)nc(-c4cccc(C(F)(F)F)n4)n3)ccn2)CC1] |
| 582 | 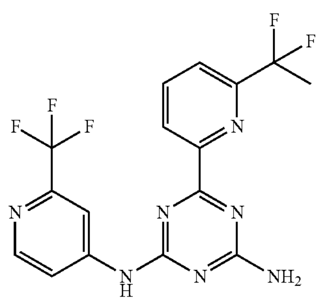 [SMILES: CC(F)(F)c1cccc(-c2nc(N)nc(Nc3ccnc(C(F)(F)F)c3)n2)n1] |
| 583 | 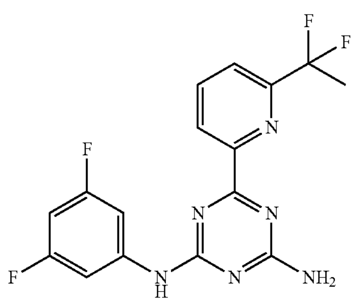 [SMILES: CC(F)(F)c1cccc(-c2nc(N)nc(Nc3cc(F)cc(F)c3)n2)n1] |
| 586 | 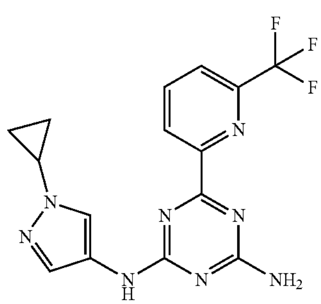 [SMILES: Nc1nc(Nc2cnn(C3CC3)c2)nc(-c2cccc(C(F)(F)F)n2)n1] |

TABLE 1-continued

Representative Compounds

| Cmpd No | Structure |
|---------|-----------|
| 592 | 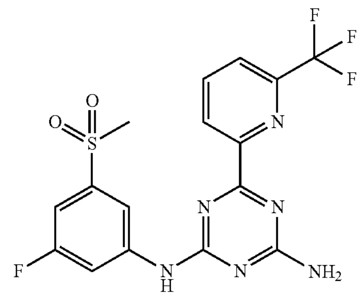 [SMILES: CS(=O)(=O)c1cc(F)cc(Nc2nc(N)nc(-c3cccc(C(F)(F)F)n3)n2)c1] |
| 594 | 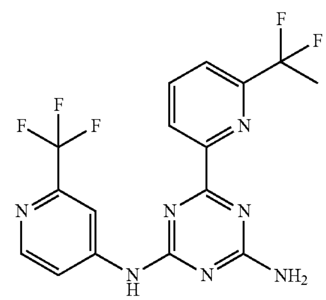 |
| 596 | 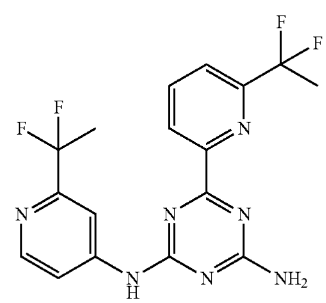 |
| 598 | 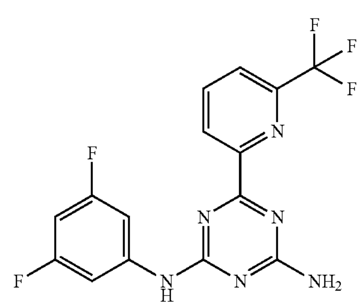 [SMILES: Nc1nc(Nc2cc(F)cc(F)c2)nc(-c2cccc(C(F)(F)F)n2)n1] |
| 599 | 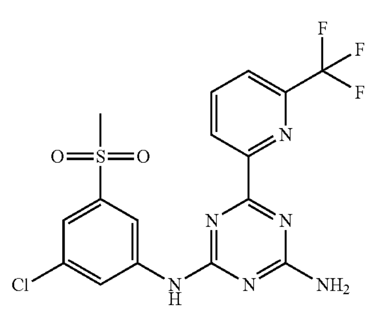 [SMILES: CS(=O)(=O)c1cc(Cl)cc(Nc2nc(N)nc(-c3cccc(C(F)(F)F)n3)n2)c1] |

TABLE 1-continued
Representative Compounds
| Cmpd No | Structure |
|---|---|
| 604 | 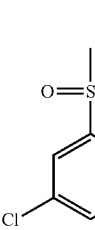 |
| 605 | 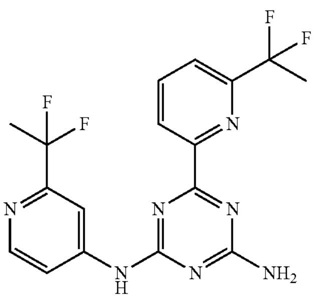 [SMILES: CC(F)(F)c1cc(Nc2nc(N)nc(-c3cccc(C(C)(F)F)n3)n2)ccn1] |
| 606 | 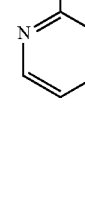 |
| 607 | 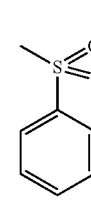 |
| 608 | 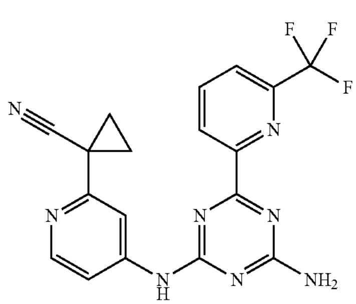 [SMILES: N#CC1(c2cc(Nc3nc(N)nc(-c4cccc(C(F)(F)F)n4)n3)ccn2)CC1] |
| 609 | 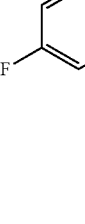 |
| 610 | 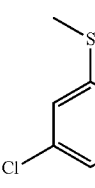 |
| 611 |  |
| 612 | |
| 614 | |

TABLE 1-continued

Representative Compounds

| Cmpd No | Structure |
|---|---|
| 618 | 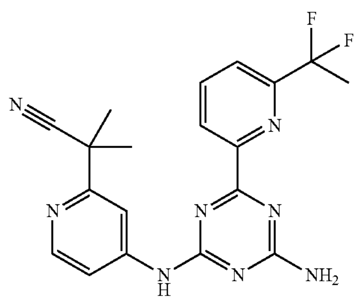 [SMILES: CC(F)(F)c1cccc(-c2nc(N)nc(Nc3ccnc(C(C)(C)C#N)c3)n2)n1] |
| 621 | 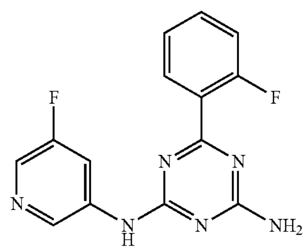 [SMILES: Nc1nc(Nc2cncc(F)c2)nc(-c2ccccc2F)n1] |
| 622 | 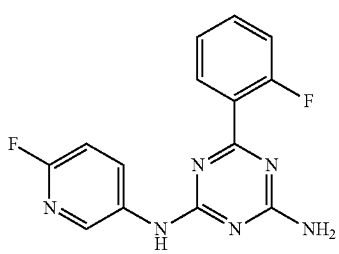 [SMILES: Nc1nc(Nc2ccc(F)nc2)nc(-c2ccccc2F)n1] |
| 623 | 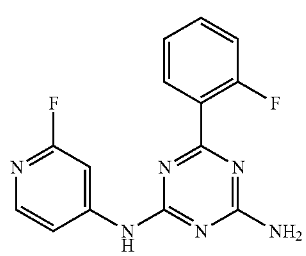 [SMILES: Nc1nc(Nc2ccnc(F)c2)nc(-c2ccccc2F)n1] |
| 624 | 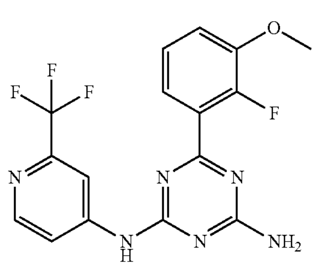 [SMILES: COc1cccc(-c2nc(N)nc(Nc3ccnc(C(F)(F)F)c3)n2)c1F] |
| 627 | 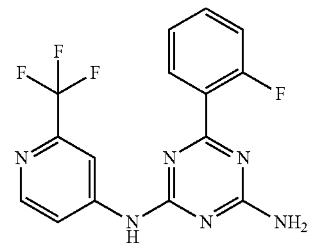 [SMILES: Nc1nc(Nc2ccnc(C(F)(F)F)c2)nc(-c2ccccc2F)n1] |
| 629 | 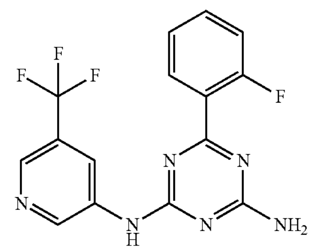 [SMILES: Nc1nc(Nc2cncc(C(F)(F)F)c2)nc(-c2ccccc2F)n1] |
| 630 | 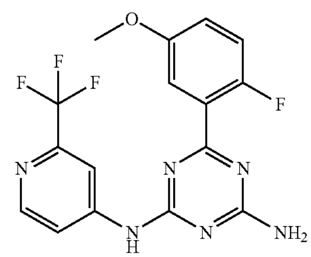 [SMILES: COc1ccc(F)c(-c2nc(N)nc(Nc3ccnc(C(F)(F)F)c3)n2)c1] |
| 632 | 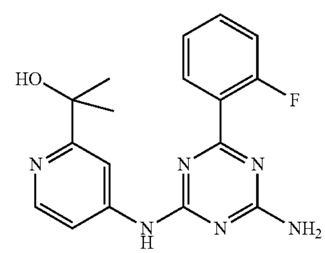 [SMILES: CC(C)(O)c1cc(Nc2nc(N)nc(-c3ccccc3F)n2)ccn1] |
| 633 | 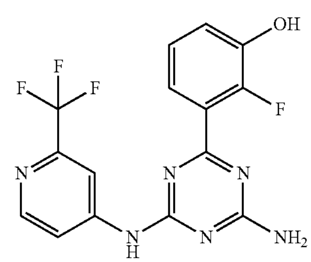 [SMILES: Nc1nc(Nc2ccnc(C(F)(F)F)c2)nc(-c2cccc(O)c2F)n1] |
| 634 | 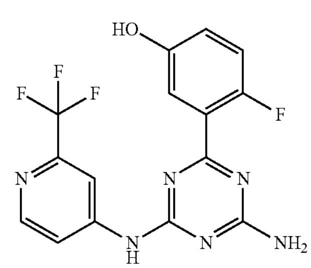 [SMILES: Nc1nc(Nc2ccnc(C(F)(F)F)c2)nc(-c2cc(O)ccc2F)n1] |

TABLE 1-continued

Representative Compounds

| Cmpd No | Structure |
|---|---|
| 635 | [structure] |
| 639 | [structure] |
| 640 | [structure] |
| 644 | [structure] |
| 645 | [structure] |
| 647 | [structure] |
| 648 | [structure] |
| 649 | [structure] |
| 650 | [structure] |
| 651 | [structure] |

TABLE 1-continued

Representative Compounds

| Cmpd No | Structure |
|---|---|
| 652 | 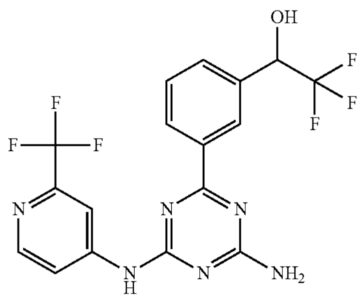 [SMILES: Nc1nc(Nc2ccnc(C(F)(F)F)c2)nc(-c2cccc(C(O)C(F)(F)F)c2)n1] |
| 653 | 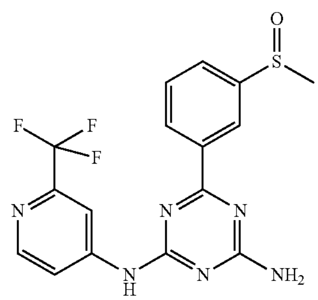 [SMILES: CS(=O)c1cccc(-c2nc(N)nc(Nc3ccnc(C(F)(F)F)c3)n2)c1] |
| 654 | 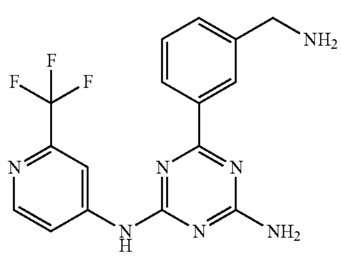 [SMILES: NCc1cccc(-c2nc(N)nc(Nc3ccnc(C(F)(F)F)c3)n2)c1] |
| 655 | 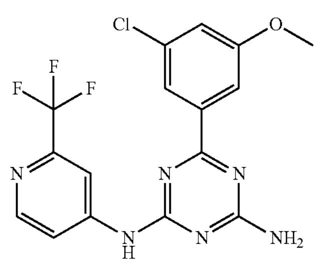 |
| 657 | 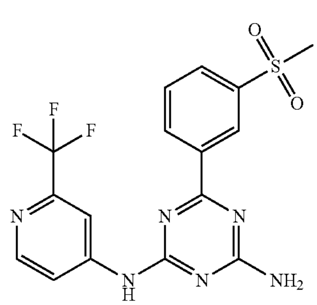 [SMILES: CS(=O)(=O)c1cccc(-c2nc(N)nc(Nc3ccnc(C(F)(F)F)c3)n2)c1] |
| 658 | |
| 662 | |
| 663 | |
| 664 | |
| 665 | |

TABLE 1-continued

Representative Compounds

| Cmpd No | Structure |
|---|---|
| 669 | (structure) |
| 670 | (structure) |
| 671 | (structure) |
| 672 | (structure) |
| 673 | (structure) |
| 674 | (structure) |
| 675 | (structure) |
| 676 | (structure) |
| 678 | (structure) |
| 682 | (structure) |

TABLE 1-continued

Representative Compounds

| Cmpd No | Structure |
|---|---|
| 683 | (structure) |
| 686 | (structure) |
| 687 | (structure) |
| 691 | (structure) |
| 696 | (structure) |

TABLE 1-continued

Representative Compounds

| Cmpd No | Structure |
|---|---|
| 697 | (structure) |

Included are methods for making compounds of Formula I or a compound of any one of the embodiments described herein comprising reacting (structure with A, B, Cl on triazine)

with NH₃. In some embodiments, the preceding methods comprise step (1) reacting (structure with A on triazine, Cl, Cl)

with

B—NH₂ to give (structure with A, B, Cl);

and step (2) reacting (structure with A, B, Cl)

with NH₃.

The compounds of one aspect of this invention may contain one or more asymmetric centers and thus occur as racemates, racemic mixtures, scalemic mixtures, and diastereomeric mixtures, as well as single enantiomers or individual stereoisomers that are substantially free from another possible enantiomer or stereoisomer. The term "substantially free of other stereoisomers" as used herein means a preparation enriched in a compound having a selected stereochemistry at one or more selected stereocenters by at least about 60%, 65%, 70%, 75%, 80%, 85%, 90%, 95%, 96%, 97%, 98%, or 99%. The term "enriched" means that at least the designated percentage of a preparation is the compound having a selected stereochemistry at one or more selected stereocenters. Methods of obtaining or synthesizing an individual enantiomer or stereoisomer for a given compound are known in the art and may be applied as practicable to final compounds or to starting material or intermediates.

In certain embodiments, the compound of Formula I or II is enriched for a structure or structures having a selected stereochemistry at one or more carbon atoms. For example, the compound is enriched in the specific stereoisomer by at least about 60%, 65%, 70%, 75%, 80%, 85%, 90%, 95%, 96%, 97%, 98%, or 99%.

The compounds of Formula I or II may also comprise one or more isotopic substitutions. For example, H may be in any isotopic form, including $^1$H, $^2$H (D or deuterium), and $^3$H (T or tritium); C may be in any isotopic form, including $^{11}$C, $^{12}$C, $^{13}$C, and $^{14}$C; N may be in any isotopic form, including $^{13}$N, $^{14}$N and $^{15}$N; O may be in any isotopic form, including $^{15}$O, $^{16}$O and $^{18}$O; F may be in any isotopic form, including $^{18}$F; and the like. For example, the compound is enriched in a specific isotopic form of H, C, N, O and/or F by at least about 60%, 65%, 70%, 75%, 80%, 85%, 90%, 95%, 96%, 97%, 98%, or 99%.

Unless otherwise indicated when a disclosed compound is named or depicted by a structure without specifying the stereochemistry and has one or more chiral centers, it is understood to represent all possible stereoisomers of the compound.

The compounds of one aspect of this invention may also be represented in multiple tautomeric forms, in such instances, one aspect of the invention expressly includes all tautomeric forms of the compounds described herein, even though only a single tautomeric form may be represented (e.g., alkylation of a ring system may result in alkylation at multiple sites, one aspect of the invention expressly includes all such reaction products; and keto-enol tautomers). All such isomeric forms of such compounds are expressly included herein.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts." J. Pharm. Sci. Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$^{2+}$, NHR$^{3+}$, NR$^{4+}$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group that may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Mesylates of each compound in Table 1 are explicitly included herein. Examples of suitable polymeric organic anions include, but are not limited to, those derived from the following polymeric acids: tannic acid, carboxymethyl cellulose.

The compounds provided herein therefore include the compounds themselves, as well as their salts, hydrates and their prodrugs, if applicable. The compounds provided herein may be modified and converted to prodrugs by appending appropriate functionalities to enhance selected biological properties, e.g., targeting to a particular tissue. Such modifications (i.e., prodrugs) are known in the art and include those which increase biological penetration into a given biological compartment (e.g., blood, lymphatic system, central nervous system), increase oral availability, increase solubility to allow administration by injection, alter metabolism and alter rate of excretion. Examples of prodrugs include esters (e.g., phosphates, amino acid (e.g., valine) esters), carbamates and other pharmaceutically acceptable derivatives, which, upon administration to a subject, are capable of providing active compounds. Calcium and sodium phosphates of each compound in Table 1, if applicable, are explicitly included herein. Amino acid (e.g., valine) esters of each compound in Table 1, if applicable, are explicitly included herein.

Compositions and Routes of Administration

The compounds utilized in the methods described herein may be formulated together with a pharmaceutically acceptable carrier or adjuvant into pharmaceutically acceptable compositions prior to be administered to a subject. In another embodiment, such pharmaceutically acceptable compositions further comprise additional therapeutic agents in amounts effective for achieving a modulation of disease or disease symptoms, including those described herein.

The term "pharmaceutically acceptable carrier or adjuvant" refers to a carrier or adjuvant that may be administered to a subject, together with a compound of one aspect of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of one aspect of this invention include, but are not limited to, ion exchangers, alumina, aluminum stearate, lecithin, self-emulsifying drug delivery systems (SEDDS)

such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of one aspect of this invention may be administered orally, parenterally, by inhalation spray, topically, rectally, nasally, buccally, vaginally or via an implanted reservoir, preferably by oral administration or administration by injection. The pharmaceutical compositions of one aspect of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of one aspect of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of one aspect of this invention may also be administered in the form of suppositories for rectal administration. These compositions can be prepared by mixing a compound of one aspect of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of one aspect of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of one aspect of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of one aspect of this invention may also be topically applied to the lower intestinal tract by rectal suppository formulation or in a suitable enema formulation. Topically-transdermal patches are also included in one aspect of this invention.

The pharmaceutical compositions of one aspect of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of one aspect of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of one aspect of this invention. Alternatively, those agents may be part of a single dosage form, mixed together with the compounds of one aspect of this invention in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of one aspect of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition or combination of one aspect of this invention may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

The pharmaceutical compositions described above comprising a compound of Structural Formula I or II or a compound described in any one of the embodiments herein, may further comprise another therapeutic agent useful for treating cancer.

Methods of Use

The inhibitory activities of the compounds provided herein against IDH2 mutants (e.g., IDH2R140Q and IDH2R172K) can be tested by methods described in Example A or analogous methods.

Provided is a method for inhibiting a mutant IDH2 activity comprising contacting a subject in need thereof with a compound of Structural Formula I or II, a compound described in any one of the embodiments herein, or a pharmaceutically acceptable salt thereof. In one embodiment, the cancer to be treated is characterized by a mutant allele of IDH2 wherein the IDH2 mutation results in a new ability of the enzyme to catalyze the NADPH-dependent reduction of α-ketoglutarate to R(−)-2-hydroxyglutarate in a subject. In one aspect of this embodiment, the mutant IDH2 has an R140X mutation. In another aspect of this embodiment, the R140X mutation is a R140Q mutation. In another aspect of this embodiment, the R140X mutation is a R140W mutation. In another aspect of this embodiment, the R140X mutation is a R140L mutation. In another aspect of this embodiment, the mutant IDH2 has an R172X mutation. In another aspect of this embodiment, the R172X mutation is a R172K mutation. In another aspect of this embodiment, the R172X mutation is a R172G mutation.

Also provided are methods of treating a cancer characterized by the presence of a mutant allele of IDH2 comprising the step of administering to subject in need thereof (a) a compound of Structural Formula I or II, a compound described in any one of the embodiments herein, or a pharmaceutically acceptable salt thereof, or (b) a pharmaceutical composition comprising (a) and a pharmaceutically acceptable carrier.

In one embodiment, the cancer to be treated is characterized by a mutant allele of IDH2 wherein the IDH2 mutation results in a new ability of the enzyme to catalyze the NADPH-dependent reduction of α-ketoglutarate to R(−)-2-hydroxyglutarate in a patient. In one aspect of this embodiment, the mutant IDH2 has an R140X mutation. In another aspect of this embodiment, the R140X mutation is a R140Q mutation. In another aspect of this embodiment, the R140X mutation is a R140W mutation. In another aspect of this embodiment, the R140X mutation is a R140L mutation. In another aspect of this embodiment, the mutant IDH2 has an R172X mutation. In another aspect of this embodiment, the R172X mutation is a R172K mutation. In another aspect of this embodiment, the R172X mutation is a R172G mutation. A cancer can be analyzed by sequencing cell samples to determine the presence and specific nature of (e.g., the changed amino acid present at) a mutation at amino acid 140 and/or 172 of IDH2.

Without being bound by theory, applicants believe that mutant alleles of IDH2 wherein the IDH2 mutation results in a new ability of the enzyme to catalyze the NAPH-dependent reduction of α-ketoglutarate to R(−)-2-hydroxyglutarate, and in particular R140Q and/or R172K mutations of IDH2, characterize a subset of all types of cancers, without regard to their cellular nature or location in the body. Thus, the compounds and methods of one aspect of this invention are useful to treat any type of cancer that is characterized by the presence of a mutant allele of IDH2 imparting such activity and in particular an IDH2 R140Q and/or R172K mutation.

In one aspect of this embodiment, the efficacy of cancer treatment is monitored by measuring the levels of 2HG in the subject. Typically levels of 2HG are measured prior to treatment, wherein an elevated level is indicated for the use of the compound of Formula I or II or a compound described in any one of the embodiments described herein to treat the cancer. Once the elevated levels are established, the level of 2HG is determined during the course of and/or following termination of treatment to establish efficacy. In certain embodiments, the level of 2HG is only determined during the course of and/or following termination of treatment. A reduction of 2HG levels during the course of treatment and following treatment is indicative of efficacy. Similarly, a determination that 2HG levels are not elevated during the course of or following treatment is also indicative of efficacy. Typically, the these 2HG measurements will be utilized together with other well-known determinations of efficacy of cancer treatment, such as reduction in number and size of tumors and/or other cancer-associated lesions, improvement in the general health of the subject, and alterations in other biomarkers that are associated with cancer treatment efficacy.

2HG can be detected in a sample by LC/MS. The sample is mixed 80:20 with methanol, and centrifuged at 3,000 rpm for 20 minutes at 4 degrees Celsius. The resulting supernatant can be collected and stored at −80 degrees Celsius prior to LC-MS/MS to assess 2-hydroxyglutarate levels. A variety of different liquid chromatography (LC) separation methods can be used. Each method can be coupled by negative electrospray ionization (ESI, −3.0 kV) to triple-quadrupole mass spectrometers operating in multiple reaction monitoring (MRM) mode, with MS parameters optimized on infused metabolite standard solutions. Metabolites can be separated by reversed phase chromatography using 10 mM tributyl-amine as an ion pairing agent in the aqueous mobile phase, according to a variant of a previously reported method (Luo et al. *J Chromatogr A* 1147, 153-64, 2007). One method allows resolution of TCA metabolites: t=0, 50% B; t=5, 95% B; t=7, 95% B; t=8, 0% B, where B refers to an organic mobile phase of 100% methanol. Another method is specific for 2-hydroxyglutarate, running a fast linear gradient from 50%-95% B (buffers as defined above) over 5 minutes. A Synergi Hydro-RP, 100 mm×2 mm, 2.1 μm particle size (Phenomenex) can be used as the column, as described above. Metabolites can be quantified by comparison of peak areas with pure metabolite standards at known concentration. Metabolite flux studies from $^{13}$C-glutamine can be performed as described, e.g., in Munger et al. Nat Biotechnol 26, 1179-86, 2008.

In one embodiment 2HG is directly evaluated.

In another embodiment a derivative of 2HG formed in process of performing the analytic method is evaluated. By way of example such a derivative can be a derivative formed in MS analysis. Derivatives can include a salt adduct, e.g., a Na adduct, a hydration variant, or a hydration variant which is also a salt adduct, e.g., a Na adduct, e.g., as formed in MS analysis.

In another embodiment a metabolic derivative of 2HG is evaluated. Examples include species that build up or are elevated, or reduced, as a result of the presence of 2HG, such as glutarate or glutamate that will be correlated to 2HG, e.g., R-2HG.

Exemplary 2HG derivatives include dehydrated derivatives such as the compounds provided below or a salt adduct thereof:

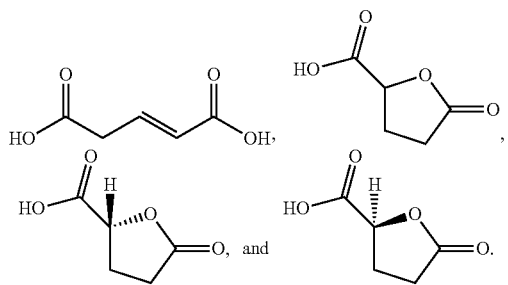

In one embodiment the cancer is a tumor wherein at least 30, 40, 50, 60, 70, 80 or 90% of the tumor cells carry an IDH2 mutation, and in particular an IDH2 R140Q, R140W, or R140L and/or R172K or R172G mutation, at the time of diagnosis or treatment.

In another embodiment, one aspect of the invention provides a method of treating a cancer selected from glioblastoma (glioma), myelodysplastic syndrome (MDS), myeloproliferative neoplasm (MPN), acute myelogenous leukemia (AML), sarcoma, melanoma, non-small cell lung cancer, chondrosarcoma, cholangiocarcinomas or angioimmunoblastic lymphoma in a patient by administering to the patient a compound of Formula I or Formula II in an amount effective to treat the cancer. In a more specific embodiment the cancer to be treated is glioma, myelodysplastic syndrome (MDS), myeloproliferative neoplasm (MPN), acute myelogenous leukemia (AML), melanoma, chondrosarcoma, or angioimmunoblastic non-Hodgkin's lymphoma (NHL).

In another embodiment, the methods described herein are used to treat glioma (glioblastoma), acute myelogenous leukemia, sarcoma, melanoma, non-small cell lung cancer (NSCLC), cholangiocarcinomas (e.g., intrahepatic cholangiocarcinoma (IHCC)), chondrosarcoma, myelodysplastic syndromes (MDS), myeloproliferative neoplasm (MPN), prostate cancer, chronic myelomonocytic leukemia (CMML), B-acute lymphoblastic leukemias (B-ALL), B-acute lymphoblastic leukemias (B-ALL), myeloid sarcoma, multiple myeloma, lymphoma colon cancer, or angioimmunoblastic non-Hodgkin's lymphoma (NHL) in a patient. In another embodiment, the cancer to be treated is an advanced hematologic malignancy selected from lymphoma (e.g., Non-Hodgkin lymphoma (NHL) such B-cell lymphoma (e.g., Burkitt lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma, and mantle cell lymphoma) and T-cell lymphoma (e.g., mycosis fungoides, anaplastic large cell lymphoma, and precursor T-lymphoblastic lymphoma).

2HG is known to accumulate in the inherited metabolic disorder 2-hydroxyglutaric aciduria. This disease is caused by deficiency in the enzyme 2-hydroxyglutarate dehydrogenase, which converts 2HG to α-KG (Struys, E. A. et al. Am J Hum Genet 76, 358-60 (2005)). Patients with 2-hydroxyglutarate dehydrogenase deficiencies accumulate 2HG in the brain as assessed by MRI and CSF analysis, develop leukoencephalopathy, and have an increased risk of developing brain tumors (Aghili, M., Zahedi, F. & Rafiee, J Neurooncol 91, 233-6 (2009); Kolker, S., Mayatepek, E. & Hoffmann, G. F. Neuropediatrics 33, 225-31 (2002); Wajner, M., Latini, A., Wyse, A. T. & Dutra-Filho, C. S. J Inherit Metab Dis 27, 427-48 (2004)). Furthermore, elevated brain levels of 2HG result in increased ROS levels (Kolker, S. et al. Eur J Neurosci 16, 21-8 (2002); Latini, A. et al. Eur J Neurosci 17, 2017-22 (2003)), potentially contributing to an increased risk of cancer. The ability of 2HG to act as an NMDA receptor agonist may contribute to this effect (Kolker, S. et al. Eur J Neurosci 16, 21-8 (2002)). 2HG may also be toxic to cells by competitively inhibiting glutamate and/or αKG utilizing enzymes. These include transaminases which allow utilization of glutamate nitrogen for amino and nucleic acid biosynthesis, and αKG-dependent prolyl hydroxylases such as those which regulate Hif1-alpha levels.

Thus, according to another embodiment, one aspect of the invention provides a method of treating 2-hydroxyglutaric aciduria, particularly D-2-hydroxyglutaric aciduria, in a patient by administering to the patient a compound of Structural Formula I or II or a compound described in any one of the embodiments described herein.

Treatment methods described herein can additionally comprise various evaluation steps prior to and/or following treatment with a compound of Structural Formula I or II or a compound described in any one of the embodiments described herein.

In one embodiment, prior to and/or after treatment with a compound of Structural Formula I or II or a compound described in any one of the embodiments described herein, the method further comprises the step of evaluating the growth, size, weight, invasiveness, stage and/or other phenotype of the cancer.

In one embodiment, prior to and/or after treatment with a compound of Formula I or II or a compound described in any one of the embodiments described herein, the method further comprises the step of evaluating the IDH2 genotype of the cancer. This may be achieved by ordinary methods in the art, such as DNA sequencing, immuno analysis, and/or evaluation of the presence, distribution or level of 2HG.

In one embodiment, prior to and/or after treatment with a compound of Formula I or II or a compound described in any one of the embodiments described herein, the method further comprises the step of determining the 2HG level in the subject. This may be achieved by spectroscopic analysis, e.g., magnetic resonance-based analysis, e.g., MRI and/or MRS measurement, sample analysis of bodily fluid, such as serum, bone marrow, blood, urine, or spinal cord fluid analysis, or by analysis of surgical material, e.g., by mass-spectroscopy.

Combination Therapies

In some embodiments, the methods described herein comprise the additional step of co-administering to a subject in need thereof a second therapy e.g., an additional cancer therapeutic agent or an additional cancer treatment. Exemplary additional cancer therapeutic agents include for example, chemotherapy, targeted therapy, antibody therapies, immunotherapy, and hormonal therapy. Additional cancer treatments include, for example: surgery, and radiation therapy. Examples of each of these treatments are provided below.

The term "co-administering" as used herein with respect to an additional cancer therapeutic agents means that the additional cancer therapeutic agent may be administered together with a compound of one aspect of this invention as part of a single dosage form (such as a composition of one aspect of this invention comprising a compound of one aspect of the invention and an second therapeutic agent as described above) or as separate, multiple dosage forms. Alternatively, the additional cancer therapeutic agent may be administered prior to, consecutively with, or following the administration of a compound of one aspect of this invention. In such combination therapy treatment, both the compounds of one aspect of this invention and the second therapeutic agent(s) are administered by conventional methods. The administration of a composition of one aspect of this invention, comprising both a compound of one aspect of the invention and a second therapeutic agent, to a subject does not preclude the separate administration of that same therapeutic agent, any other second therapeutic agent or any compound of one aspect of this invention to said subject at another time during a course of treatment. The term "co-administering" as used herein with respect to an additional cancer treatment means that the additional cancer treatment may occur prior to, consecutively with, concurrently with or following the administration of a compound of one aspect of this invention.

In some embodiments, the additional cancer therapeutic agent is a chemotherapy agent. Examples of chemotherapeutic agents used in cancer therapy include, for example, antimetabolites (e.g., folic acid, purine, and pyrimidine derivatives), alkylating agents (e.g., nitrogen mustards, nitrosoureas, platinum, alkyl sulfonates, hydrazines, triazenes, aziridines, spindle poison, cytotoxic agents, topoisomerase inhibitors and others), and hypomethylating agents (e.g., decitabine (5-aza-deoxycytidine), zebularine, isothiocyanates, azacitidine (5-azacytidine), 5-flouro-2'-deoxycytidine, 5,6-dihydro-5-azacytidine and others). Exemplary agents include Aclarubicin, Actinomycin, Alitretinoin, Altretamine, Aminopterin, Aminolevulinic acid, Amrubicin, Amsacrine, Anagrelide, Arsenic trioxide, Asparaginase, Atrasentan, Belotecan, Bexarotene, bendamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy.

In some embodiments, the additional cancer therapeutic agent is a differentiation agent. Such differentiation agent includes retinoids (such as all-trans-retinoic acid (ATRA), 9-cis retinoic acid, 13-cis-retinoic acid (13-cRA) and 4-hydroxy-phenretinamide (4-HPR)); arsenic trioxide; histone deacetylase inhibitors HDACs (such as azacytidine (Vidaza) and butyrates (e.g., sodium phenylbutyrate)); hybrid polar compounds (such as hexamethylene bisacetamide ((HMBA)); vitamin D; and cytokines (such as colony-stimulating factors including G-CSF and GM-CSF, and interferons).

In some embodiments the additional cancer therapeutic agent is a targeted therapy agent. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, dasatinib, erlotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (HERCEPTIN®) typically used in breast cancer, and the anti-CD20 antibody rituximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein, e.g., a biguanide such as metformin or phenformin, preferably phenformin.

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

In some embodiments, the additional cancer therapeutic agent is an immunotherapy agent. Cancer immunotherapy refers to a diverse set of therapeutic strategies designed to induce the subject's own immune system to fight the tumor. Contemporary methods for generating an immune response against tumors include intravesicular BCG immunotherapy for superficial bladder cancer, and use of interferons and other cytokines to induce an immune response in renal cell carcinoma and melanoma subjects.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound or composition described herein.

In some embodiments, the additional cancer therapeutic agent is a hormonal therapy agent. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a compound or a composition described herein.

Other possible additional therapeutic modalities include imatinib, gene therapy, peptide and dendritic cell vaccines, synthetic chlorotoxins, and radiolabeled drugs and antibodies.

EXAMPLES

Abbreviations

| | |
|---|---|
| anhy.—anhydrous | δ—chemical shift |
| aq.—aqueous | J—coupling constant |
| min—minute(s) | s—singlet |
| mL—milliliter | d—doublet |
| mmol—millimole(s) | t—triplet |
| mol—mole(s) | q—quartet |
| MS—mass spectrometry | m—multiplet |
| NMR—nuclear magnetic resonance | br—broad |
| TLC—thin layer chromatography | qd—quartet of doublets |
| HPLC—high-performance liquid chromatography | dquin—doublet of quintets |
| | dd—doublet of doublets |
| Hz—hertz | dt—doublet of triplets |
| CHCl$_3$—chloroform | NaHCO$_3$—sodium bicarbonate |
| DCM—dichloromethane | LiHMDS—lithium hexamethyldisilylamide |
| DMF—dimethylformamide | |
| Et$_2$O—diethyl ether | NaHMDS—sodium hexamethyldisilylamide |
| EtOH—ethyl alcohol | |
| EtOAc—ethyl acetate | LAH—lithium aluminum hydride |
| MeOH—methyl alcohol | NaBH$_4$—sodium borohydride |
| MeCN—acetonitrile | LDA—lithium diisopropylamide |
| PE—petroleum ether | Et$_3$N—triethylamine |
| THF—tetrahydrofuran | DMAP—4-(dimethylamino)pyridine |
| AcOH—acetic acid | DIPEA —N,N-diisopropylethylamine |
| HCl—hydrochloric acid | NH4OH—ammonium hydroxide |
| H$_2$SO$_4$—sulfuric acid | EDCI—1-ethyl-3-(3-dimethylaminopropyl)carbodiimide |
| NH$_4$Cl—ammonium chloride | |
| KOH—potassium hydroxide | HOBt—1-hydroxybenzotriazole |
| NaOH—sodium hydroxide | HATU—O-(7-azabenzotriazol-1-yl)-N,N,N'N'-tetra-methyluronium |
| K$_2$CO$_3$—potassium carbonate | |
| Na$_2$CO$_3$—sodium carbonate | BINAP—2,2'-bis(diphenylphosphanyl)-1,1'-binaphthyl |
| TFA—trifluoroacetic acid | |
| Na$_2$SO$_4$—sodium sulfate | |
| NaBH$_4$—sodium borohydride | |

Reagents that may be used herein are purchased from commercial sources and can be used without further purification. Nuclear magnetic resonance (NMR) spectra are obtained on a Brucker AMX-400 NMR (Brucker, Switzerland). Chemical shifts were reported in parts per million (ppm, δ) downfield from tetramethylsilane. Mass spectra are run with electrospray ionization (ESI) from a Waters LCT TOF Mass Spectrometer (Waters, USA).

For exemplary compounds disclosed in this section, the specification of a stereoisomer (e.g., an (R) or (S) stereoisomer) indicates a preparation of that compound such that the compound is enriched at the specified stereocenter by at least about 90%, 95%, 96%, 97%, 98%, or 99%. The chemical name of each of the exemplary compound described below is generated by ChemDraw software. Compounds of Formula I may be prepared by methods known in the art, for example, by following analogous procedures described in the International Patent Application PCT/CN2013/000009 and U.S. patent application Ser. No. 13/735,467.

Example 1

Preparation of Intermediates for Preparing Compounds of Formula I Wherein A is Phenyl

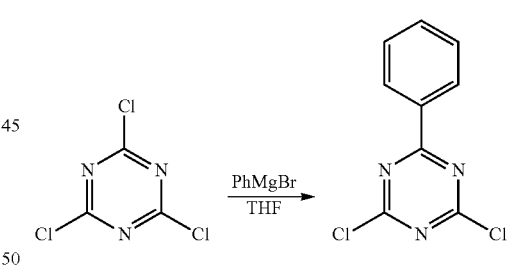

Preparation of 2,4-dichloro-6-phenyl-1,3,5-triazine

To a solution of 2,4,6-trichloro-[1,3,5]triazine (120 g, 0.652 mol) in anhydrous THF (1200 mL) was added phenylmagnesium bromide (217 mL, 0.651 mol, 3 M in ether) dropwise at −10 to −0° C. under N$_2$ protection. After the addition, the mixture was warmed to room temperature and stirred for 2 hrs. The reaction was cooled to 0° C. and quenched by addition of saturated NH$_4$Cl (200 mL), then extracted with ethyl acetate. The organic layer was dried, concentrated and purified via column chromatography (eluted with petroleum ether) to afford 2,4-dichloro-6-phenyl-1,3,5-triazine as a white solid. $^1$H NMR (CDCl$_3$) δ 7.51-7.55 (m, 2H), 7.64-7.67 (m, 1H), 8.49-8.63 (m, 2H).

Example 2

Preparation of Intermediates for Preparing Compounds of Formula I Wherein Ring A is Substituted Pyridin-2-Yl

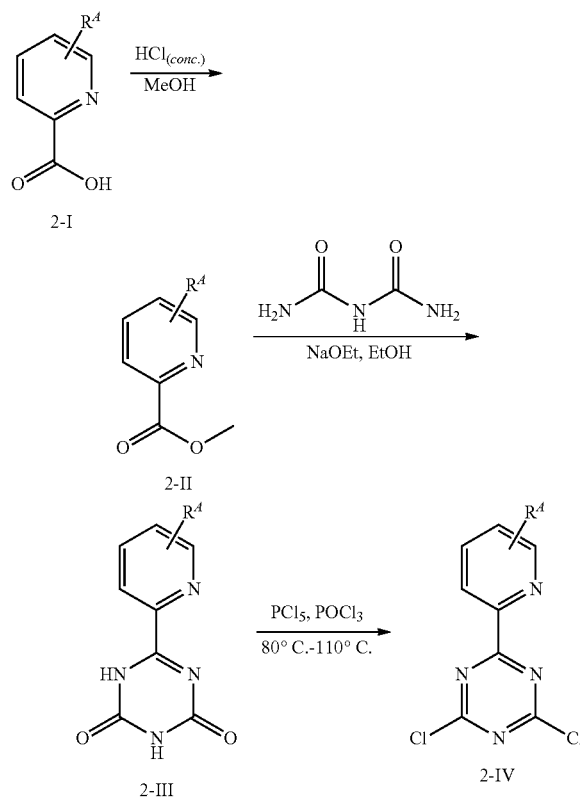

Step 1: Preparation of 6-chloro-pyridine-2-carboxylic acid methyl ester (2-11)

To a solution of 6-chloro-pyridine-2-carboxylic acid (48 g, 0.31 mol) in methanol (770 ml) was added concentrated HCl (6 ml). The mixture was stirred at 80° C. for 48 hours then concentrated to remove the volatile. The crude product was diluted with ethyl acetated and washed with Sat. NaHCO₃ solution. The organic layer was dried with anhydrous Na₂SO₄ and concentrated to give 6-chloro-pyridine-2-carboxylic acid methyl ester as a white solid.

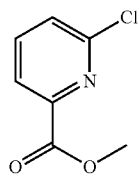

LC-MS: m/z 172.0 (M+H)⁺.

The procedure set forth in Step 1 was used to produce the following intermediates (2-II) using the appropriate starting material 2-I.

6-trifluoromethyl-pyridine-2-carboxylic acid methyl ester

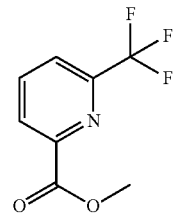

LC-MS: m/z 206 (M+H)⁺.

Step 2: Preparation of 6-(6-chloropyridin-2-yl)-1,3,5-triazine-2,4-dione

To a solution of Na (32 g, 0.16 mol) in ethanol (500 mL) was added methyl 6-chloropicolinate (32 g, 0.16 mol) and biuret (5.3 g, 0.052 mol). The mixture was heated to reflux for 1 hour. Then concentrated to give residue which was poured to water and added Sat.NaHCO₃ solution to adjust pH to 7, the precipitated solid was collected by filtration and dried to give 6-(6-chloropyridin-2-yl)-1,3,5-triazine-2,4-dione.

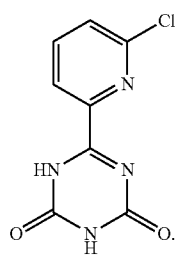 [SMILES: O=c1nc(-c2cccc(Cl)n2)[nH]c(=O)[nH]1]

LC-MS: m/z 225 (M+H)⁺.

Step 2 was used to produce the following intermediates (2-III) starting with appropriate intermediate 2-II.

6-(6-trifluoromethyl-pyridin-2-yl)-1H-1,3,5-triazine-2,4-dione as a pale white solid.

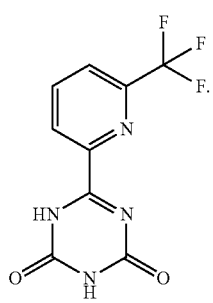 [SMILES: O=c1nc(-c2cccc(C(F)(F)F)n2)[nH]c(=O)[nH]1]

LC-MS: m/z 259 (M+H)⁺.

6-pyridin-2-yl-1H-1,3,5-triazine-2,4-dione

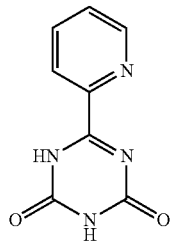

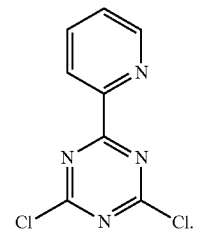

LC-MS: m/z 227.0 (M+H)⁺.

¹H NMR (DMSO-d4): δ 11.9-12.5 (s, 1H), 11.3-11.6 (s, 1H), 8.7-8.9 (m, 1H), 8.2-8.4 (m, 1H), 8.0-8.2 (m, 1H), 7.6-7.8 (m, 1H).

Step 3: Preparation of 2,4-dichloro-6-(6-chloropyridin-2-yl)-1,3,5-triazine

To a solution of 6-(pyridin-2-yl)-1,3,5-triazine-2,4(1H,3H)-dione (3.0 g, 013 mol) in POCl₃ (48 mL) was added PCl₅ (23 g, 0.1 mol). The mixture was stirred at 100° C. for 2 hours then concentrated to remove the volatile. The residue was diluted with ethyl acetated and washed with Sat.NaHCO₃ solution. The organic layer was dried over anhydrous Na₂SO₄ and concentrated to give 2,4-dichloro-6-(6-chloropyridin-2-yl)-1,3,5-triazine as a brown solid.

Example 3

Preparation of Compounds of Formula I Wherein Ring A is Substituted Aryl or Heteroaryl

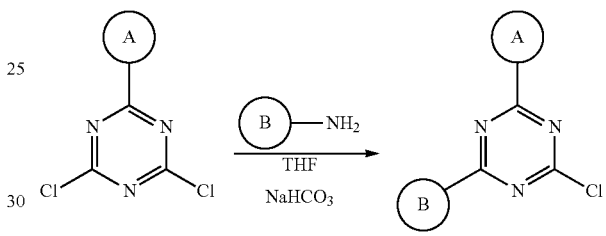

Preparation of 4-chloro-6-(4-trifluoromethyl-pyrimidin-2-yl)-[1,3,5]triazin-2-yl]-(2-trifluoromethyl-pyridin-4-yl)-amine To a solution of 2,4-dichloro-6-(4-(trifluoromethyl)pyrimidin-2-yl)-1,3,5-triazine (981 mg, 3.31 mmol) in THF (80 mL) was added 2-(trifluoromethyl)pyridin-4-amine (590 mg, 3.64 mmol) and NaHCO₃ (556 mg, 6.6 mmol). The mixture was stirred at refluxing for 18 hours. The mixture was concentrated and poured to water, extracted with ethyl acetate, dried over sodium sulphate, filtered and concentrated to give a residue, which was purified by SiO₂ chromatography to give 4-chloro-6-(4-trifluoromethyl-pyrimidin-2-yl)-[1,3,5]triazin-2-yl]-(2-trifluoromethyl-pyridin-4-yl)-amine.

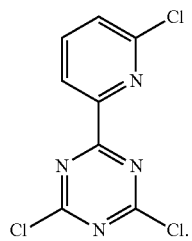

LC-MS: m/z 260.9 (M+H)⁺.

The procedure set forth in Step 3 together with the appropriate starting intermediate 2-III was used to produce the following intermediates (2-IV).

2,4-dichloro-6-(6-trifluoromethyl-pyridin-2-yl)-1,3,5-triazine as light yellow solid.

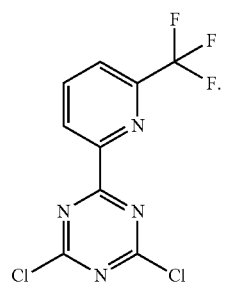 [SMILES: FC(F)(F)c1cccc(-c2nc(Cl)nc(Cl)n2)n1]

LC-MS: m/z 294.9 (M+H)⁺.

2,4-Dichloro-6-pyridin-2-yl-[1,3,5]triazine (1.0 g, 80%) as brown solid.

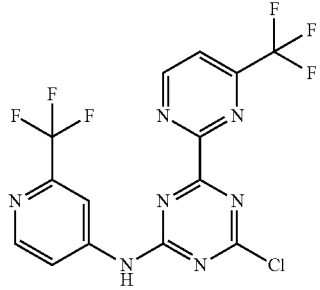 [SMILES: FC(F)(F)c1cc(Nc2nc(Cl)nc(-c3nccc(C(F)(F)F)n3)n2)ccn1]

LCMS: m/z 422.2 (M+H)⁺

The following intermediate was similarly prepared accordingly:

4-chloro-6-(6-(trifluoromethyl)pyridin-2-yl)-N-(2-(trifluoromethyl)pyridin-4-yl)-1,3,5-triazin-2-amine

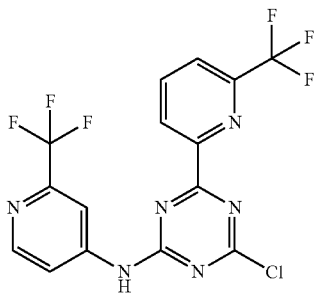 [SMILES: FC(F)(F)c1cc(Nc2nc(Cl)nc(-c3cccc(C(F)(F)F)n3)n2)ccn1]

LCMS: m/z 421.2 (M+H)+

4-chloro-6-(6-(1,1-difluoroethyl)pyridin-2-yl)-N-(2-(trifluoromethyl)pyridin-4-yl)-1,3,5-triazin-2-amine

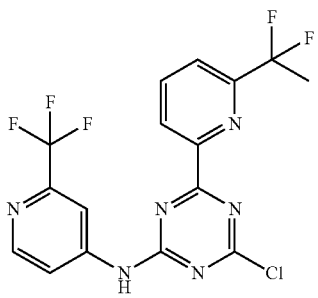 [SMILES: CC(F)(F)c1cccc(-c2nc(Cl)nc(Nc3ccnc(C(F)(F)F)c3)n2)n1]

LCMS: m/z 416.3 (M+H)+

Example 4

Preparation of 6-(6-(trifluoromethyl)pyridin-2-yl)-N2-(2-(trifluoromethyl)pyridin-4-yl)-1,3,5-triazine-2,4-diamine (Compound 378)

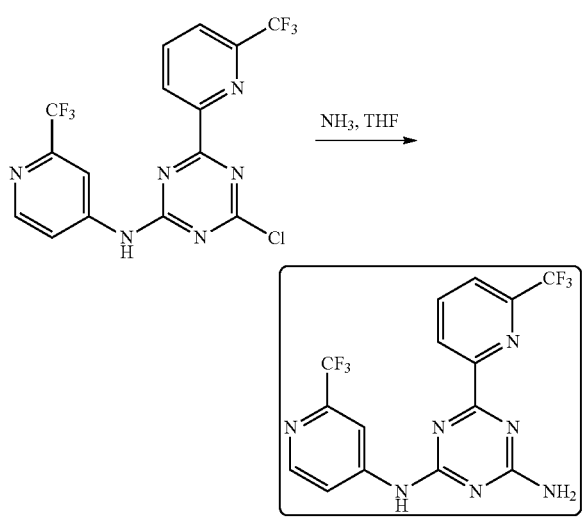

To $NH_3$ in THF (10%, 15 ml) was added 4-chloro-6-(6-(trifluoromethyl)pyridin-2-yl)-N-(2-(trifluoromethyl)pyridin-4-yl)-1,3,5-triazin-2-amine (2.0 g, 4.76 mmol), a precipitate was formed at the same time. After stirring for another 2 h, the solid was filtered and dried to give the desired product 1.6 g (yield: 82%). MW (402.2, M+1). $^1$H NMR (400 MHz, MeOH-d) δ: 8.71 (d, J=7.8 Hz, 1H), 8.52 (d, J=5.1 Hz, 1H), 8.38 (br. s., 1H), 8.24 (t, J=7.5 Hz, 1H), 8.18 (br. s., 1H), 8.01 (d, J=7.8 Hz, 1H).

Example A

Enzymatic and Cell Assays

Enzymatic Assay.

Compounds are assayed for IDH2 R172K inhibitory activity through a cofactor depletion assay. Compounds are preincubated with enzyme, then the reaction is started by the addition of NADPH and α-KG, and allowed to proceed for 60 minutes under conditions previously demonstrated to be linear with respect for time for consumption of both cofactor and substrate. The reaction is terminated by the addition of a second enzyme, diaphorase, and a corresponding substrate, resazurin. Diaphorase reduces resazurin to the highly fluorescent resorufin with the concomitant oxidation of NADPH to NADP, both halting the IDH2 reaction by depleting the available cofactor pool and facilitating quantitation of the amount of cofactor remaining after a specific time period through quantitative production of an easily detected fluorophore.

Specifically, into each of 12 wells of a 384-well plate, 1 µl of 100× compound dilution series is placed, followed by the addition of 40 µl of buffer (50 mM potassium phosphate ($K_2HPO_4$), pH 7.5; 150 mM NaCl; 10 mM $MgCl_2$, 10% glycerol, 0.05% bovine serum albumin, 2 mM beta-mercaptoethanol) containing 1.25 µg/ml IDH2 R172K. The test compound is then incubated for one hour at room temperature with the enzyme; before starting the IDH2 reaction with the addition of 10 µl of substrate mix containing 50 µM NADPH and 6.3 mM α-KG in the buffer described above. After a further one hour of incubation at room temperature, the reaction is halted and the remaining NADPH measured through conversion of resazurin to resorufin by the addition of 25 µl Stop Mix (36 µg/ml diaphorase enzyme and 60 µM resazurin; in buffer). After one minute of incubation the plate is read on a plate reader at Ex544/Em590.

For determination of the inhibitory potency of compounds against IDH2 R140Q in an assay format similar to the above, a similar procedure is performed, except that the final testing concentration is 0.25 µg/ml IDH2 R140Q protein, 4 µM NADPH and 1.6 mM α-KG, and the preincubation time is one hour or sixteen hours.

For determination of the inhibitory potency of compounds against IDH2 R140Q in a high throughput screening format, a similar procedure is performed, except that 0.25 µg/ml IDH2 R140Q protein was utilized in the preincubation step, and the reaction is started with the addition of 4 µM NADPH and 8 µM α-KG.

U87MG pLVX-IDH2 R140Q-neo Cell Based Assay.

U87MG pLVX-IDH2 R140Q-neo cells are grown in T125 flasks in DMEM containing 10% FBS, 1× penicillin/streptomycin and 500 µg/mL G418. They are harvested by trypsin and seeded into 96 well white bottom plates at a density of 5000 cell/well in 100 µl/well in DMEM with 10% FBS. No cells are plated in columns 1 and 12. Cells are incubated overnight at 37° C. in 5% $CO_2$. The next day compounds are made up at 2× concentration and 100 ul are added to each cell well. The final concentration of DMSO is 0.2% and the DMSO control wells are plated in row G. The plates are then placed in the incubator for 48 hours. At 48 hours, 100 ul of media is removed from each well and analyzed by LC-MS for 2-HG concentrations. The cell plate is placed back in the incubator for another 24 hours. At 72 hours post compound addition, 10 mL/plate of Promega Cell Titer Glo reagent is thawed and mixed. The cell plate is removed from the incubator and allowed to equilibrate to room temperature. Then 100 ul of reagent is added to each well of media. The cell plate is then placed on an orbital shaker for 10 minutes and then allowed to sit at room temperature for 20 minutes. The plate is then read for luminescence with an integration time of 500 ms to determine compound effects on growth inhibition.

Representative compound 378 was tested in R140Q enzymatic assay (16 hours preincubation time) and R140Q cell-based assay as described above or similar thereto, having an IC50 less than 50 nM in both assays.

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A compound having Formula II:

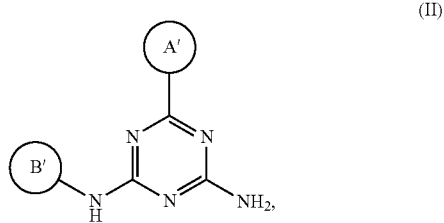

(II)

or a pharmaceutically acceptable salt thereof, wherein:
ring A' is selected from phenyl, pyrimidin-2-yl, pyrimidin-4-yl, pyrimidin-5-yl, oxazol-4-yl, isoxazol-3-yl, thiazol-2-yl, pyridin-3-yl and pyridin-2-yl, wherein ring A' is optionally substituted with one or two substituents independently selected from 1-propenyl, -cyclopropyl-OH, chloro, fluoro, —CF$_3$, —CHF$_2$, —CH$_3$, —CH$_2$CH$_3$, —CF$_2$CH$_3$, —S(O)CH$_3$, —S(O)$_2$CH$_3$, —CH$_2$OH, —CH(OH)CH$_3$, —CH(OH)CF$_3$, —OH, —OCH$_3$, —OCH$_2$CH$_3$, —C(O)—NH$_2$, —CH$_2$NH$_2$, —NH(CH$_3$), —CN and —N(CH$_3$)$_2$; and
ring B' is selected from phenyl, pyridin-3-yl, pyridin-4-yl, pyridazin-4-yl, isoxazol-4-yl, isoxazol-3-yl, thiazol-5-yl, pyrimidin-5-yl and pyrazol-4-yl, wherein ring B' is optionally substituted with one to two substituents independently selected from halo; —CN; —OH; C$_1$-C$_4$ alkyl optionally substituted with halo, CN or —OH; —S(O)$_2$—C$_1$-C$_4$ alkyl; —S(O)—C$_1$-C$_4$ alkyl; —S(O)$_2$—NH—C$_1$-C$_4$ alkyl; —S(O)$_2$—NH—CH$_2$—CF$_3$; —S(O)$_2$—N(C$_1$-C$_4$ alkyl)$_2$; —S(O)$_2$-azetidin-1-yl; —O—C$_1$-C$_4$ alkyl; —CH$_2$—O—CH$_3$, morpholin-4-yl, cyclopropyl, cyclopropyl-C$_1$-C$_4$ alkyl, cyclopropyl-C$_1$-C$_4$ alkoxy, cyclopropyl-CN; —S(O)$_2$—NH-cyclopropyl; —S(O)$_2$—NH—CH$_2$-cyclopropyl; —C(O)—C$_1$-C$_4$ alkyl, —C(O)—O—CH$_3$;

wherein:
a. ring A' and ring B' are not both an optionally substituted phenyl;
b. when ring A' is unsubstituted pyridyl, then ring B' is not phenyl optionally substituted with one to three groups independently selected from methyl, ethyl, t-butyl, methoxy, CH(OH)CH$_3$, Cl, Br, and CF$_3$;
c. when ring A' is oxazol-4-yl, isoxazol-3-yl, or thiazol-2-yl, then ring B' is not phenyl optionally substituted with one to two groups independently selected from F, Cl, SO$_2$CH$_3$, C(O)OCH$_3$, methyl, ethyl, t-butyl, methoxy, ethoxy, CF$_3$, and OH;
d. the compound is not:
 (1) N$^2$-2-pyridinyl-6-(3-pyridinyl)-1,3,5-triazine-2,4-diamine;
 (2) 6-(6-methoxy-3-pyridinyl)-N$^2$-(4-methylphenyl)-1,3,5-triazine-2,4-diamine;
 (3) 6-(2-methoxy-3-pyridinyl)-N$^2$-(4-methylphenyl)-1,3,5-triazine-2,4-diamine;
 (4) N$^2$-(3-chlorophenyl)-6-(2-chloro-4-pyridinyl)-1,3,5-triazine-2,4-diamine;
 (5) 3-[[4-[[4-amino-6-[(3-chlorophenyl)amino]-1,3,5-triazin-2-yl]-2-pyridinyl]amino]-1-propanol;
 (6) N-[34[4-amino-6-(2-methyl-4-pyrimidinyl)-1,3,5-triazin-2-yl]amino]-4-methylphenyl]-N'-[4-chloro-3-(trifluoromethyl)phenyl]-urea;
 (7) 2,6-bis[6-(2-amino-4-phenylamino-1,3,5-triazinyl)] pyridine; or
 (8) 2,6-bis[6-(2-amino-4-phenylamino-1,3,5-triazinyl)] pyrazine.

2. The compound of claim 1, wherein ring A' is selected from 2-chlorophenyl, 2-fluorophenyl, 2-methoxyphenyl, 3-hydroxyphenyl, 3-amidophenyl, 3-methylsulfinylphenyl, 3-methyl sulfonylphenyl, 3-(1-methanol)phenyl, 3-methanaminephenyl, 3-methoxy-2-fluorophenyl, 5-methoxy-2-fluorophenyl, 3-hydroxy-2-fluorophenyl, 5-hydroxy-2-fluorophenyl, 5-hydroxy-3-fluorophenyl, 3-methanolphenyl, 3,5-dihydroxyphenyl, 3-trifluoromethyl-5-chlorophenyl, 3-(1-hydoxy-2,2,2-trifluoroethyl)phenyl, 3-(1-hydoxyethyl) phenyl, 3-(1-hydoxycyclopropyl)phenyl, 3-hydroxymethyl-5-phenol, pyridin-2-yl, 3-fluoropyridin-2-yl, 3-cyanopyridin-2-yl, 3,6-difluoropyridin-2-yl, 3-fluoro-6-methoxypyridin-2-yl, 3-fluoro-6-hydroxypyridin-2-yl, 3-fluoro-6-aminopyridin-2-yl, 4-fluoro-6-aminopyridin-2-yl, 6-propen-1-ylpyridin-2-yl, 6-methylaminopyridin-2-yl, 3-fluoro-6-trifluoromethylpyridin-2-yl, 4-chloro-6-aminopyridin-2-yl, 4-fluoro-6-aminopyridin-2-yl, 4-chloro-6-methoxypyridin-2-yl, 6-aminopyridin-3-yl, 2-methoxypyridin-3-yl, 6-aminopyridin-2-yl, 6-chloropyridin-2-yl, 6-trifluoromethylpyridin-2-yl, 6-difluoromethylpyridin-2-yl, 4-(CH$_2$OH)-6-trifluoromethyl-pyridin-2-yl, 4-(CH$_2$OH)-6-chloro-pyridin-2-yl, 6-(1,1-difluoroethyl)-4-fluoropyridin-2-yl, 4-trifluoromethylpyrimidin-2-yl, 4-aminopyrimidin-2-yl, 6-trifluoromethyl-4-aminopyrimidin-2-yl, 4-trifluoromethyl-6-aminopyrimidin-2-yl, 4-aminopyrimidin-2-yl, 2-aminopyrimidin-4-yl, 2-aminopyrimidin-5-yl, 4,6-dichloropyridin-2-yl, 3,5-dichlorophenyl, 2,6-difluorophenyl, 2-methyloxazol-4-yl, 4-trifluoromethylthiazol-2-yl, 4-methylthiazol-2-yl and phenyl.

3. The compound of claim 1, wherein ring B' is selected from 2-(morpholin-4-yl)pyridin-4-yl, 3,5-difluorophenyl, 3-chlorophenyl, 3-cyanomethylphenyl, 3-cyanophenyl, 3-(cyclopropylmethyl)phenyl, 3-cyclopropylaminosulfonylphenyl, 3-dimethylaminosulfonylphenyl, 3-ethyl sulfonylphenyl, 3-fluorophenyl, 3-methyl sulfonylphenyl, 4-fluorophenyl, 3-(1-hydroxyisopropyl)phenyl, 3-methylsulfonyl-5-chlorophenyl, 3-methylsulfonyl-5-fluorophenyl, 3-(N-2,2, 2,-trifluoroethylaminosulfonyl)phenyl, 5-chloropyridin-3-yl, 5-cyanopyridin-3-yl, 5-cyanopyridin-3-yl, 5-cyanopyridin-4-yl, 5-fluoropyridin-3-yl, 5-trifluoromethylpyridin-3-yl, 2-trifluoromethylpyridin-4-yl, 2-difluoromethylpyridin-4-yl, 2-chloropyridin-4-yl, 6-chloropyridin-4-yl, 6-cyanopyridin-4-yl, 2-cyanopyridin-4-yl, 6-cyclopropylpyridin-4-yl, 6-ethoxypyridin-4-yl, 6-fluoropyridin-3-yl, 2-fluoropyridin-4-yl, 5,6-difluoropyridin-3-yl, 6-fluoropyridin-4-yl, 6-methylpyridin-4-yl, 2-difluoromethylpyridin-4-yl, 6-trifluoromethylpyridin-4-yl, 2-(1-methoxycyclopropyl)pyridin-4-yl, 2-cyclopropylpyridin-4-yl, 2-(propan-1-one)pyridin-4-yl, 2-(1-methylcyclopropyl)pyridin-4-yl, 2-(1-cyanocyclopropyl)pyridin-4-yl, 2-(1-cyanoisopropyl)pyridin-4-yl, isoxazol-4-yl, phenyl, pyridin-4-yl, picolinat-2-yl, pyrimidin-5-yl, 1-propylpyrazol-4-yl, 6-methylpyridazin-4-yl, and thiazol-5-yl.

4. The compound of claim 1, wherein the compound is

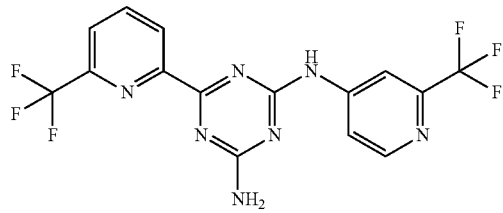 [SMILES: Nc1nc(Nc2ccnc(C(F)(F)F)c2)nc(-c2cccc(C(F)(F)F)n2)n1]

or a pharmaceutically acceptable salt thereof.

5. A pharmaceutical composition comprising the compound of claim 1, and a pharmaceutically acceptable carrier.

6. A pharmaceutical composition comprising the compound of claim 4, and a pharmaceutically acceptable carrier.

7. A method of treating a glioblastoma characterized by the presence of an IDH2 mutation, wherein the IDH2 mutation results in a new ability of the enzyme to catalyze the NADPH-dependent reduction of α-ketoglutarate to R(−)-2-hydroxyglutarate in a patient, comprising the step of administering to the patient a therapeutically effective amount of the compound of claim 1.

8. The method of claim 7, wherein the IDH2 mutation is an IDH2 R140Q or R172K mutation.

9. The method of claim 7, wherein the IDH2 mutation is an IDH2 R140Q mutation.

10. The method of claim 7, further comprising administering to the patient in need thereof a second therapeutic agent useful in the treatment of glioblastoma.

11. A method of treating a glioblastoma characterized by the presence of an IDH2 mutation, wherein the IDH2 mutation results in a new ability of the enzyme to catalyze the NADPH-dependent reduction of a-ketoglutarate to R(−)-2-hydroxyglutarate in a patient, comprising the step of administering to the patient a therapeutically effective amount of the compound of claim 2.

12. The method of claim 11, wherein the IDH2 mutation is an IDH2 R140Q or R172K mutation.

13. The method of claim 11, wherein the IDH2 mutation is an IDH2 R140Q mutation.

14. The method of claim 11, further comprising administering to the patient in need thereof a second therapeutic agent useful in the treatment of glioblastoma.

* * * * *